(12) United States Patent
Verschoor

(10) Patent No.: US 6,171,830 B1
(45) Date of Patent: *Jan. 9, 2001

(54) METHOD FOR THE ISOLATION AND PURIFICATION OF LIPID CELL-WALL COMPONENTS

(75) Inventor: Jan Adrianus Verschoor, Pretoria (ZA)

(73) Assignee: Adcock Ingram Limited, Bryanston (ZA)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/894,363

(22) PCT Filed: Feb. 22, 1996

(86) PCT No.: PCT/GB96/00416

§ 371 Date: Nov. 6, 1997

§ 102(e) Date: Nov. 6, 1997

(87) PCT Pub. No.: WO96/26288

PCT Pub. Date: Aug. 29, 1996

(30) Foreign Application Priority Data

Feb. 22, 1995 (ZA) .................................................... 95/1464

(51) Int. Cl.$^7$ ............................... C12P 7/64; C12N 1/00; G01N 33/92
(52) U.S. Cl. ............................ 435/134; 435/252; 436/71
(58) Field of Search ................................ 435/134, 243; 436/71

(56) References Cited

U.S. PATENT DOCUMENTS 4,877,612 * 10/1989 Berger et al. ........................... 424/92

FOREIGN PATENT DOCUMENTS

| 0261248 | 3/1988 | (EP) . |
| 9500163 | 1/1995 | (WO) . |
| 9528642 | 10/1995 | (WO) . |

OTHER PUBLICATIONS

Beckman et al., "Recognition of a lipid antigen by CD1–restricted T cells", Nature, Dec. 1994, vol. 372, , pp. 691–694.*

Butler et al., "High–performance liquid chromatography patterns of mycolic acids as criteria for identification of *Mycobacterium chelonae, Mycobacterium fortuitum,* and *Mycobacterium smegmatis*", Journal of Clinical Microbiology, Sep. 1990, vol. 28, no.*

Morris et al., "Counter–current distribution", In:Separation Methods in Biochemistry, Morris C.J.O.R. and Morris P., Pitman Publishing, 1976, p. 639.*

Bergey' Manual of Determinative Bacteriology, Ninth Edition, 1994, pp. 585 and 621–623.*

Fujita, Ikeda, et al Possible existence of a novel amphipathic immunostimulator in the phenol–water extracts of Mycobacteriaceae, Microbial Immunology 1987; 31 (4):289–311 Abstract.

* cited by examiner

Primary Examiner—Sandra E. Saucier
Assistant Examiner—Vera Afremova
(74) Attorney, Agent, or Firm—Ladas & Parry

(57) ABSTRACT

A method of purifying mycolic acids, salts thereof or derivatives thereof. The method involves a) providing a mixture including the mycolic acids, salts thereof or derivatives thereof and contaminants; b) dissolving the mixture in a bi-phasic solvent to form a dissolved mixture including the mycolic acids, salts thereof or derivatives thereof and contaminants; c) purifying the mycolic acids, salts thereof or derivatives thereof by subjecting the dissolved mixture to countercurrent distribution separation involving a sufficient number of cycles to separate the mycolic acids, salts thereof or derivatives thereof from the contaminants; and d) removing the separated, purified mycolic acids, salts thereof or derivatives thereof from the bi-phasic solvent. Residual impurities may be extracted from the removed mycolic acids, salts thereof or derivatives thereof with acetone.

24 Claims, 29 Drawing Sheets

FIG. 8A: CRUDE *M. TUBERCULOSIS* EXTRACT

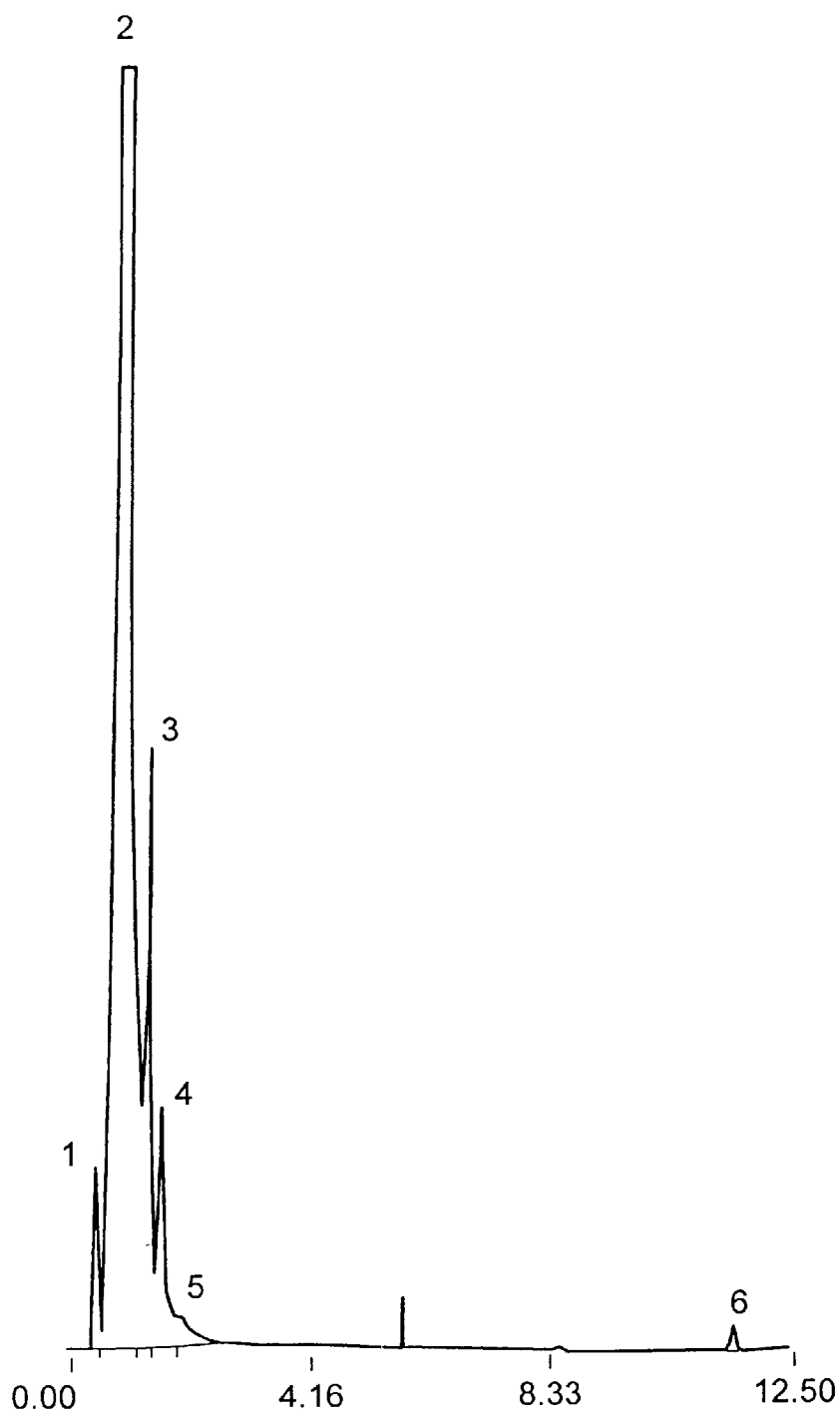
FIG. 8B: CRUDE REAGENTS EXTRACT

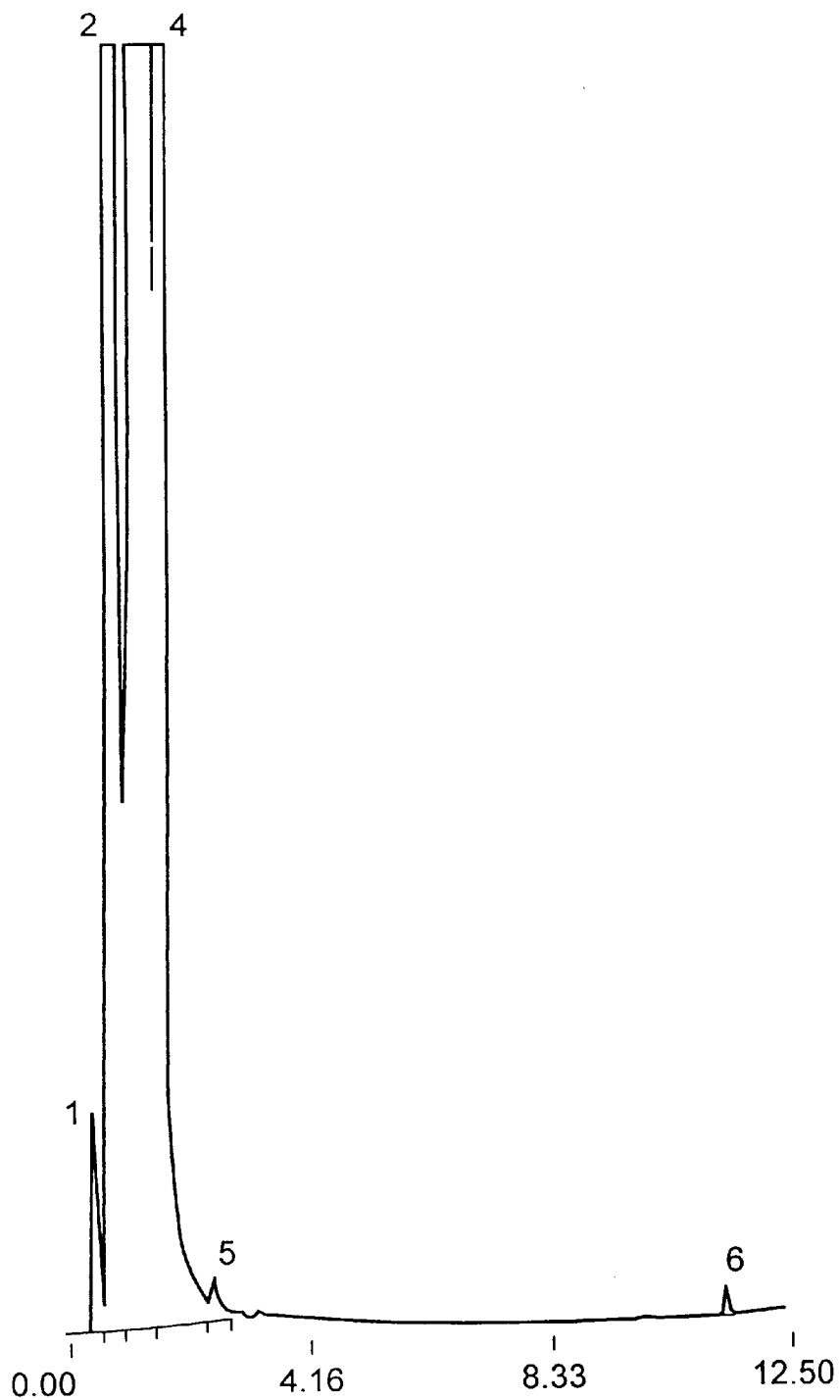
FIG. 8C: CRUDE MEDIUM EXTRACT

FIG. 9A: ACETONE SUPERNATANT OF THE
EXTRACTED CRUDE M. TUBERCULOSIS EXTRACT

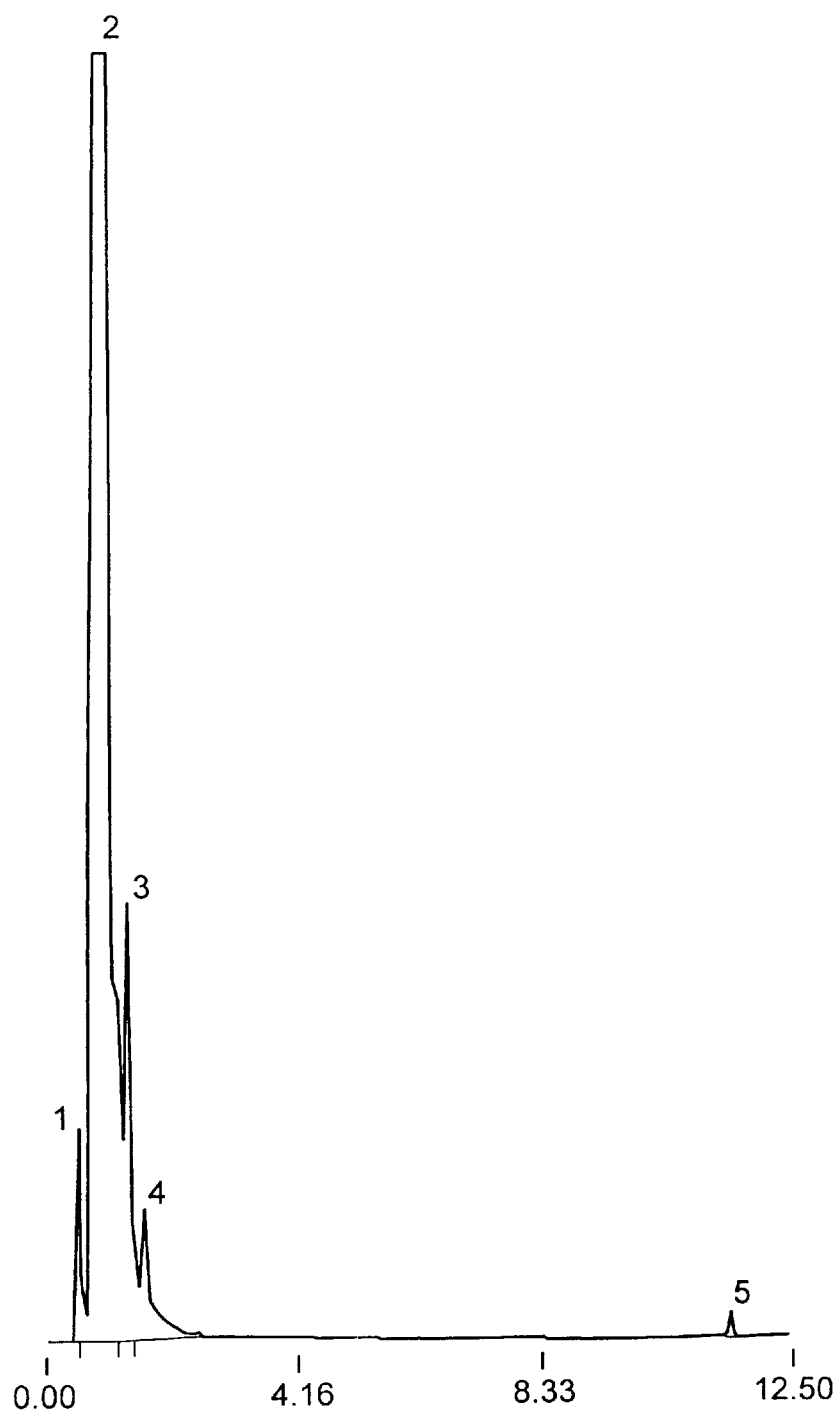
FIG. 9B: ACETONE SUPERNATANT OF THE
EXTRACTED, CRUDE REAGENTS EXTRACT

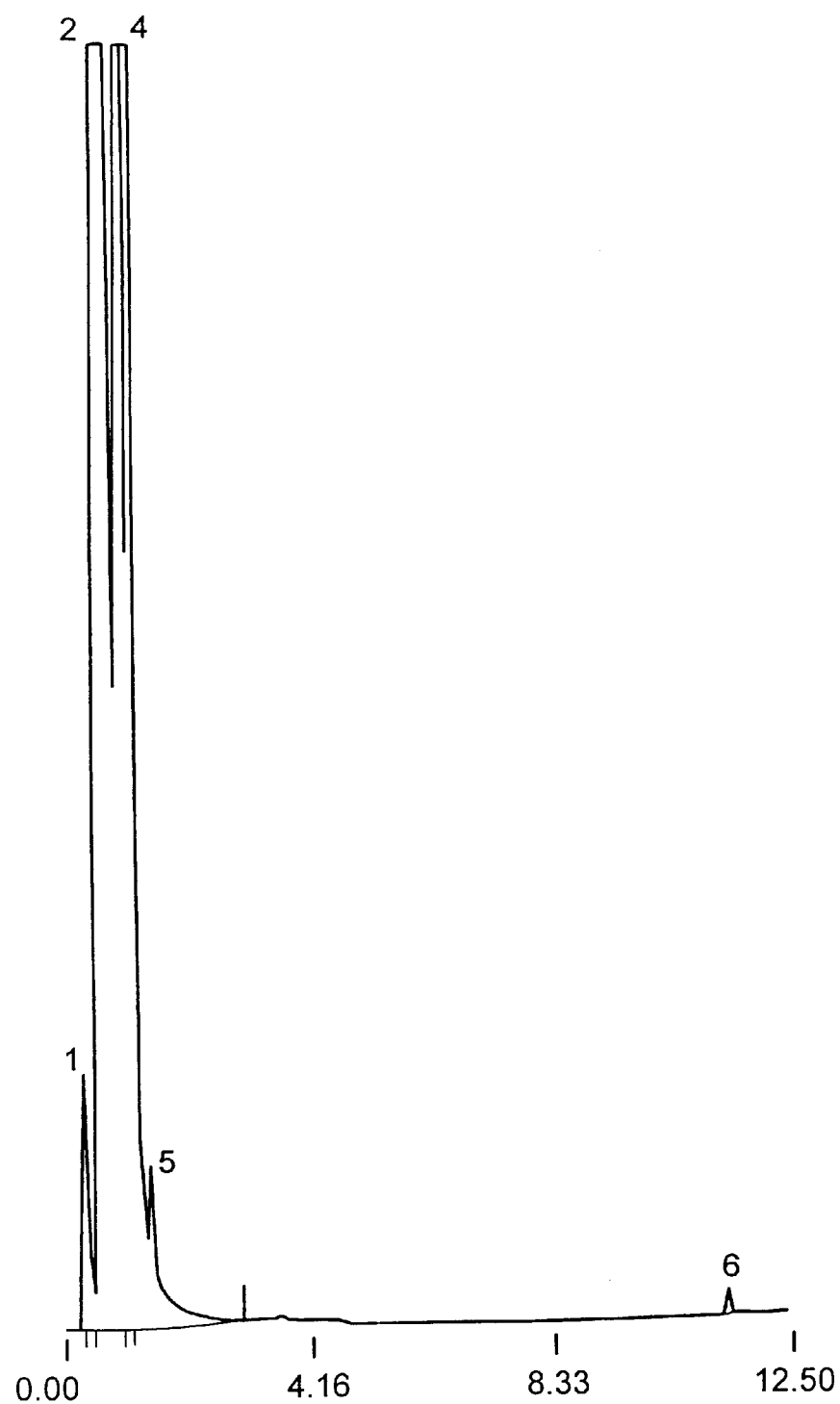
FIG. 9C: ACETONE SUPERNATANT OF THE EXTRACTED, CRUDE MEDIUM EXTRACT

FIG. 10A: CRUDE *M. TUBERCULOSIS* EXTRACT, ACETONE EXTRACTED

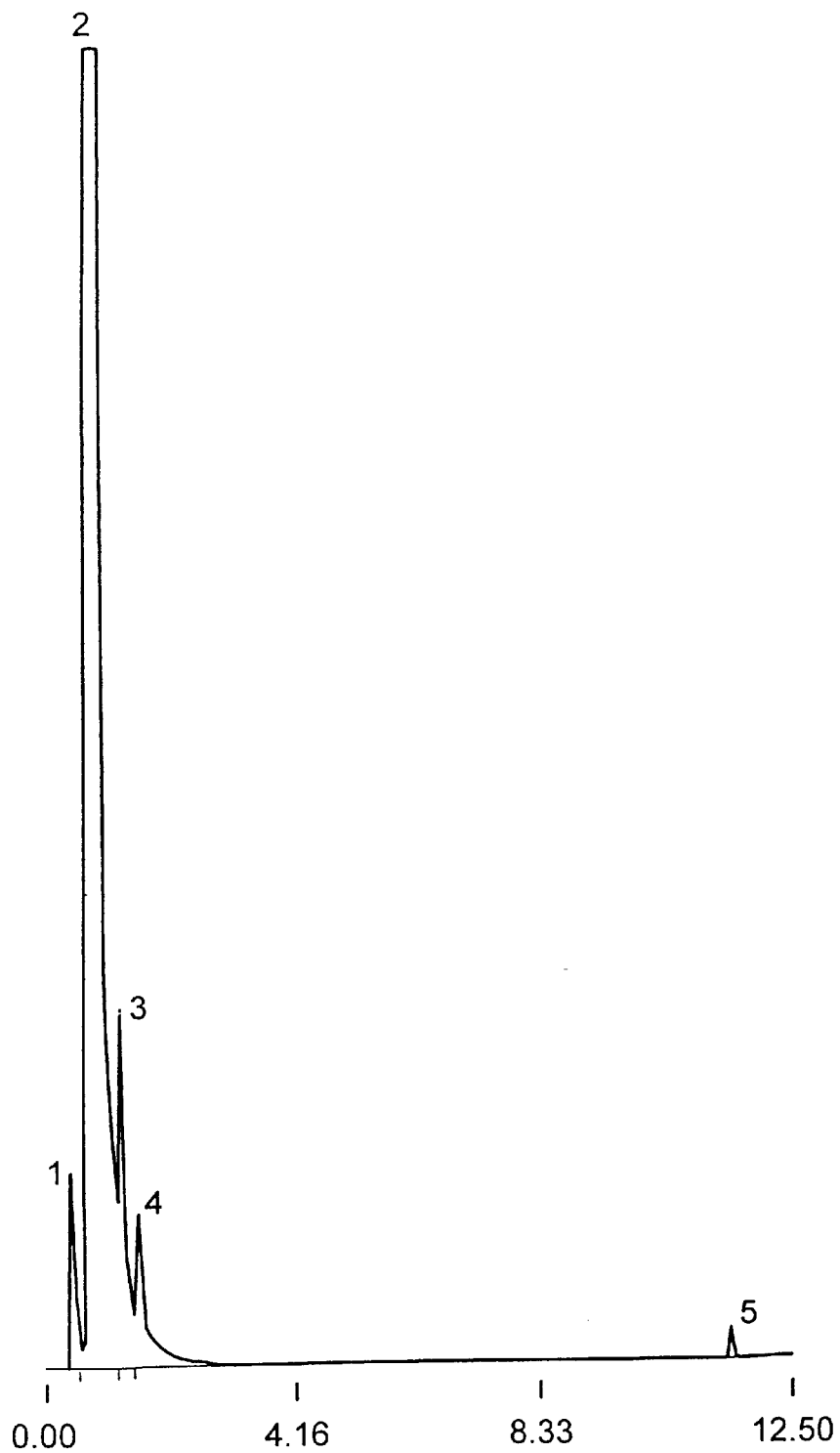
FIG. 10B: CRUDE REAGENTS EXTRACT, ACETONE EXTRACTED

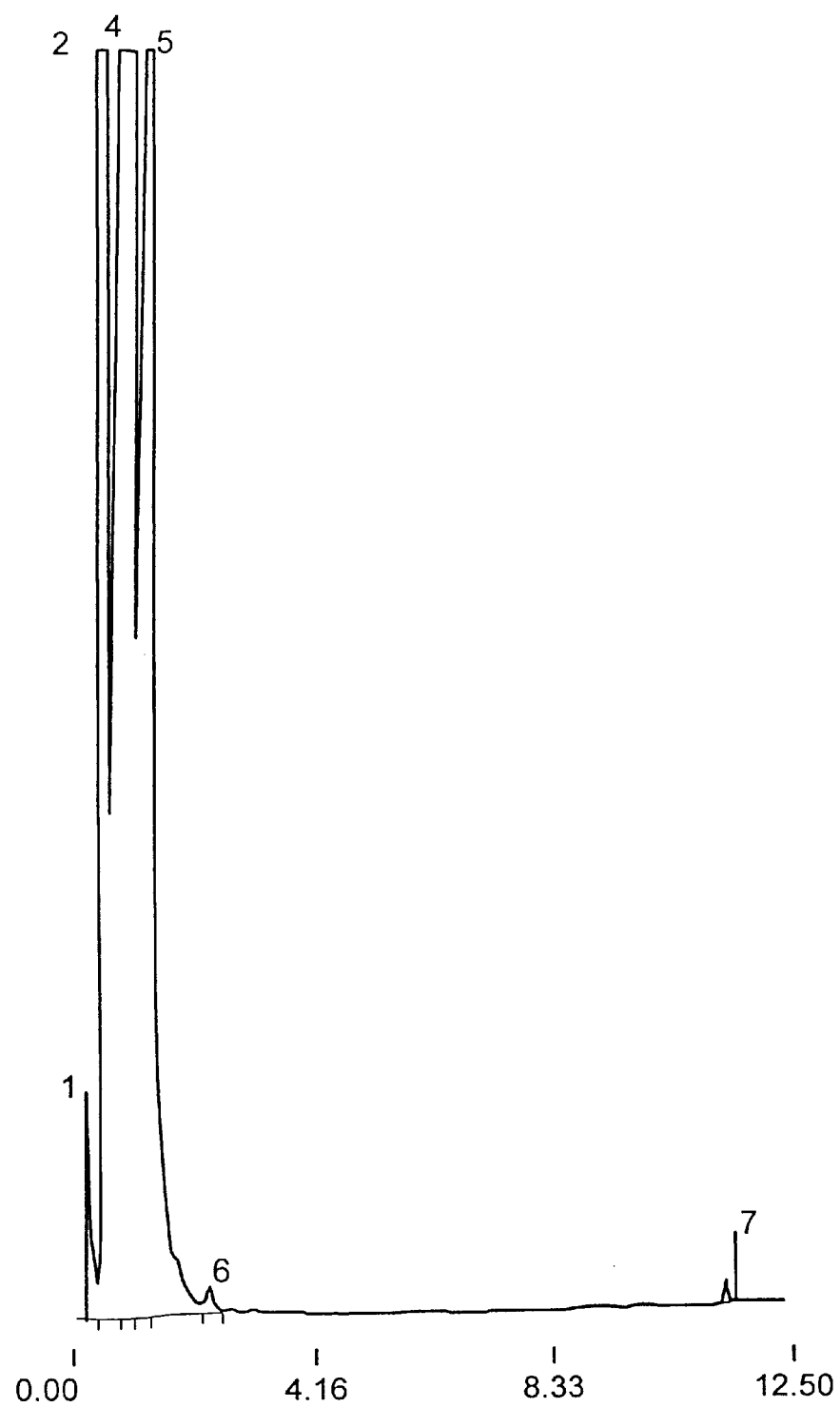
FIG. 10C: CRUDE MEDIUM EXTRACT, ACETONE EXTRACTED

F I G. 11A: COUNTERCURRENT PURIFIED
MYCOLIC ACIDS OF *M. TUBERCULOSIS*,
FROM ACETONE EXTRACTED CRUDE EXTRACT

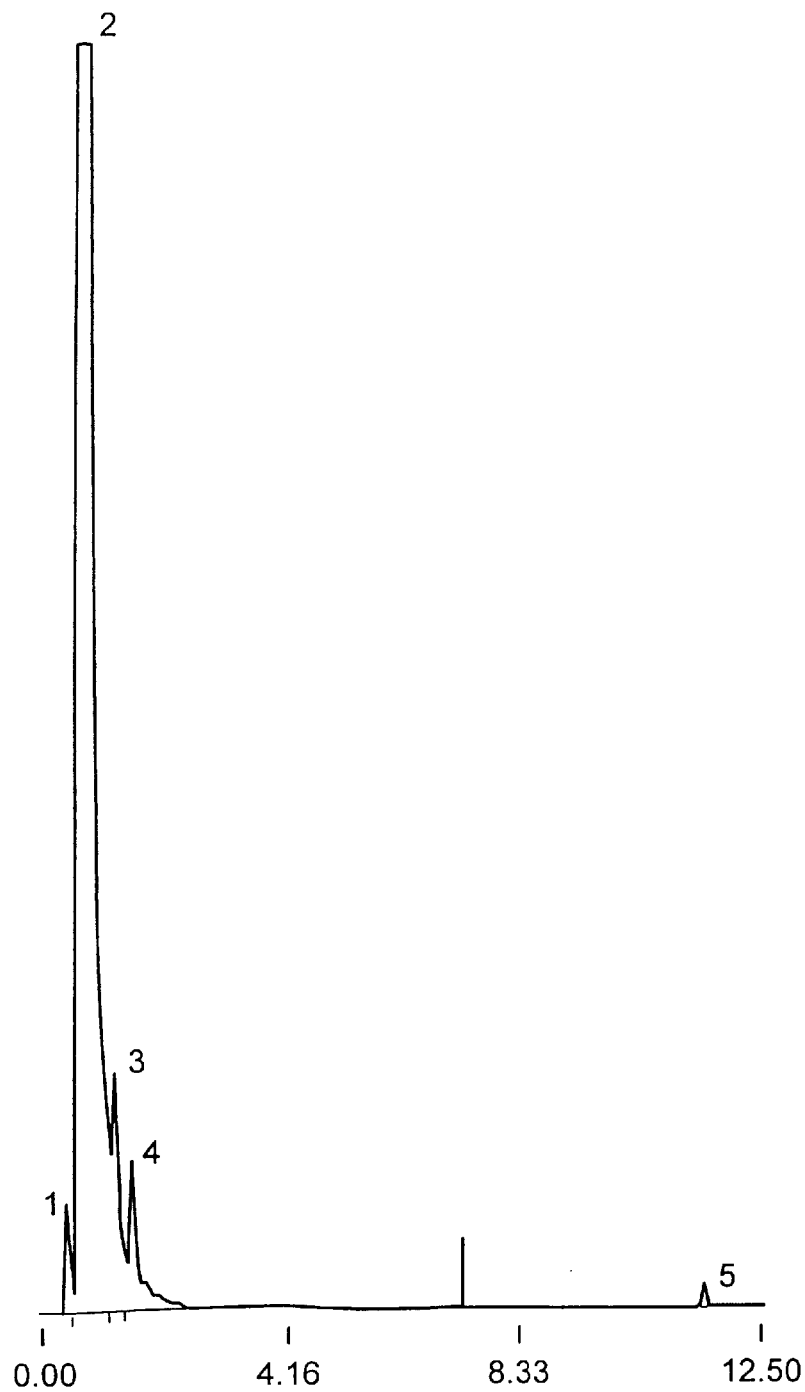
FIG. 11B: COUNTERCURRENT PURIFIED REAGENTS FROM ACETONE EXTRACTED CRUDE REAGENTS EXTRAC

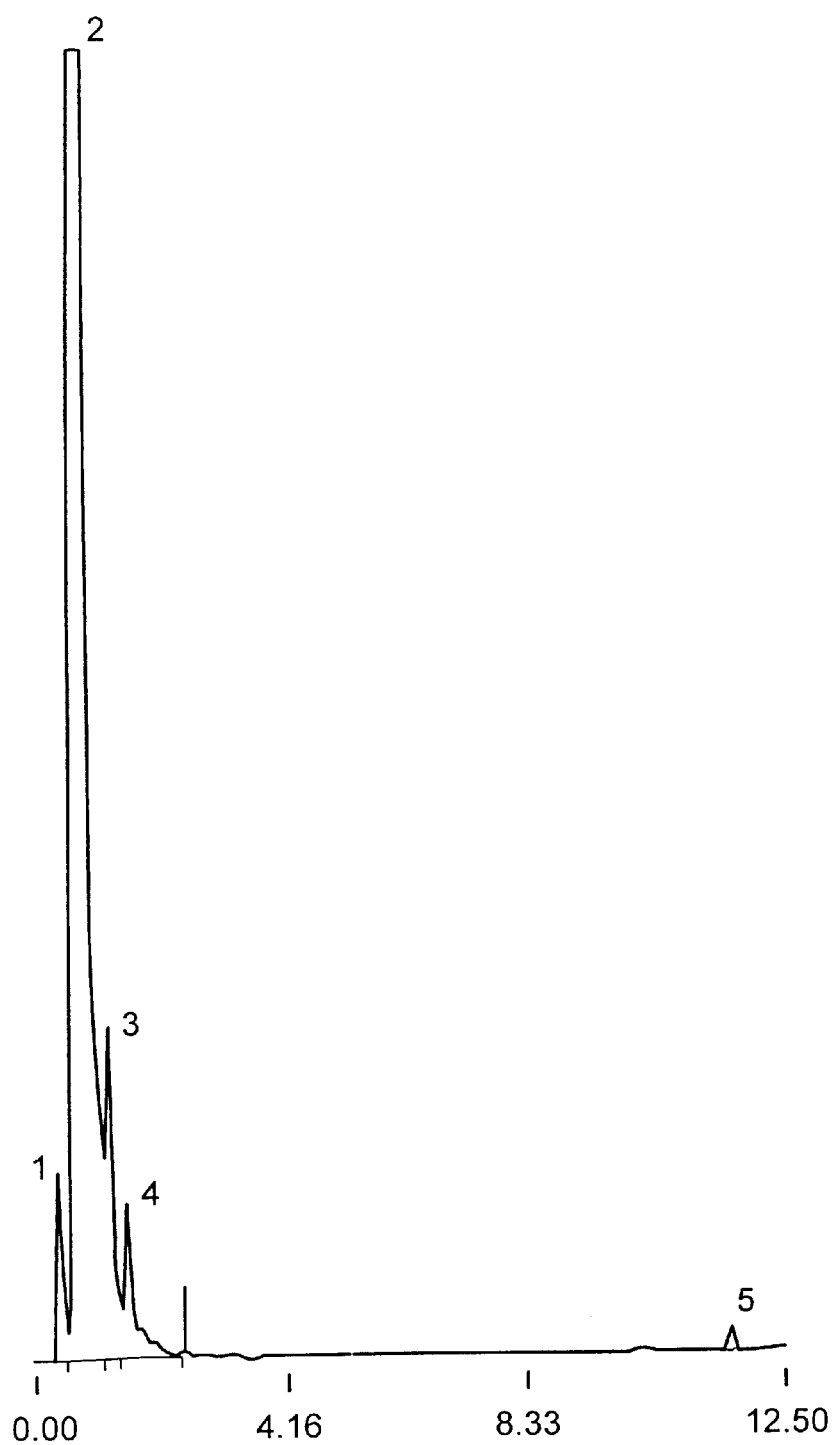
FIG. 11C: COUNTERCURRENT PURIFIED MEDIUM FROM ACETONE EXTRACTED CRUDE MEDIUM EXTRACT

FIG. 12A

COUNTERCURRENT PURIFIED MYCOLIC ACIDS
FROM CRUDE EXTRACT OF *M. TUBERCULOSIS*,
NOT EXTRACTED WITH ACETONE

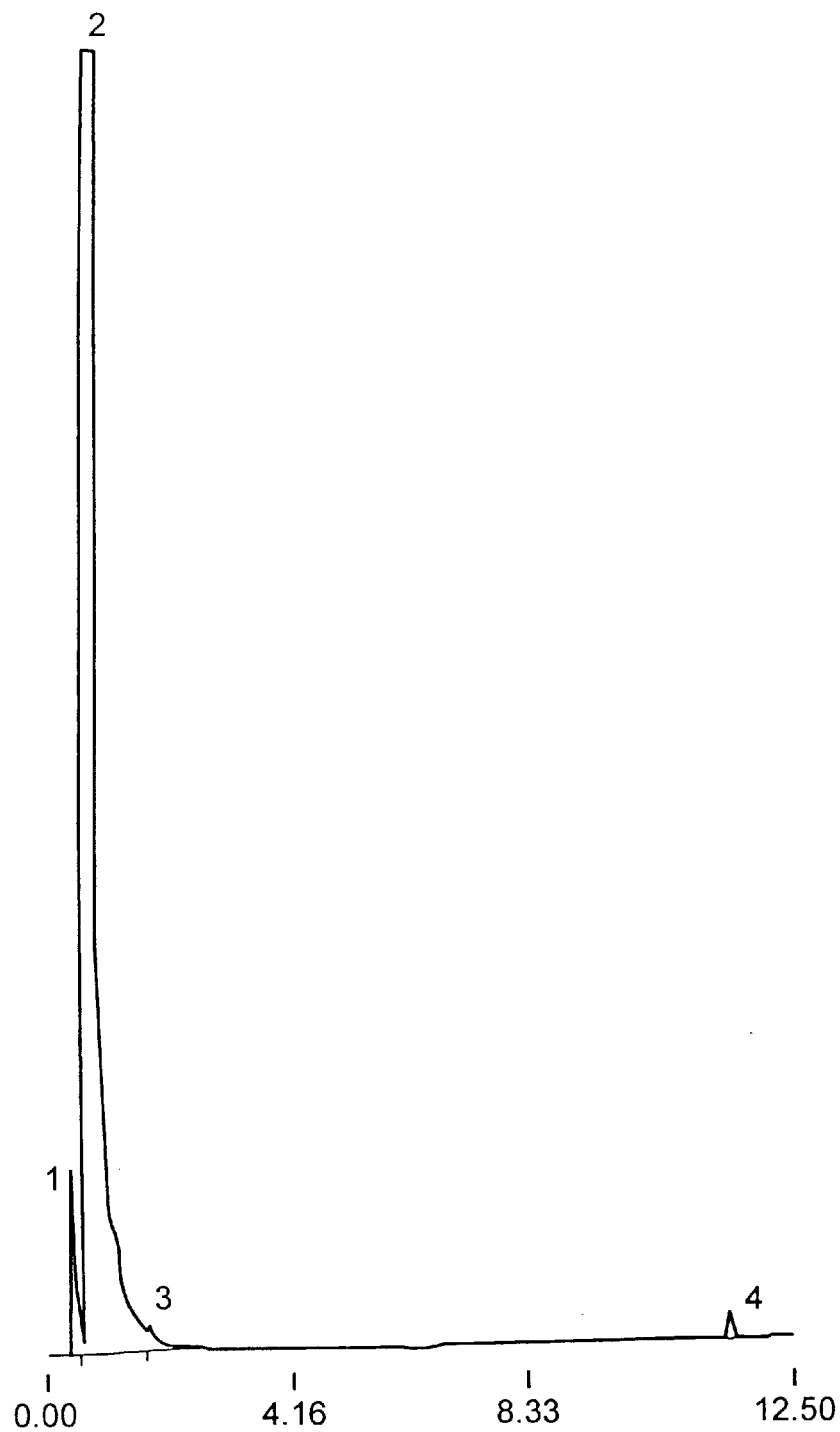
FIG. 12B: COUNTERCURRENT PURIFIED REAGENTS FROM CRUDE REAGENT EXTRACT, NOT EXTRACTED WITH ACETONE

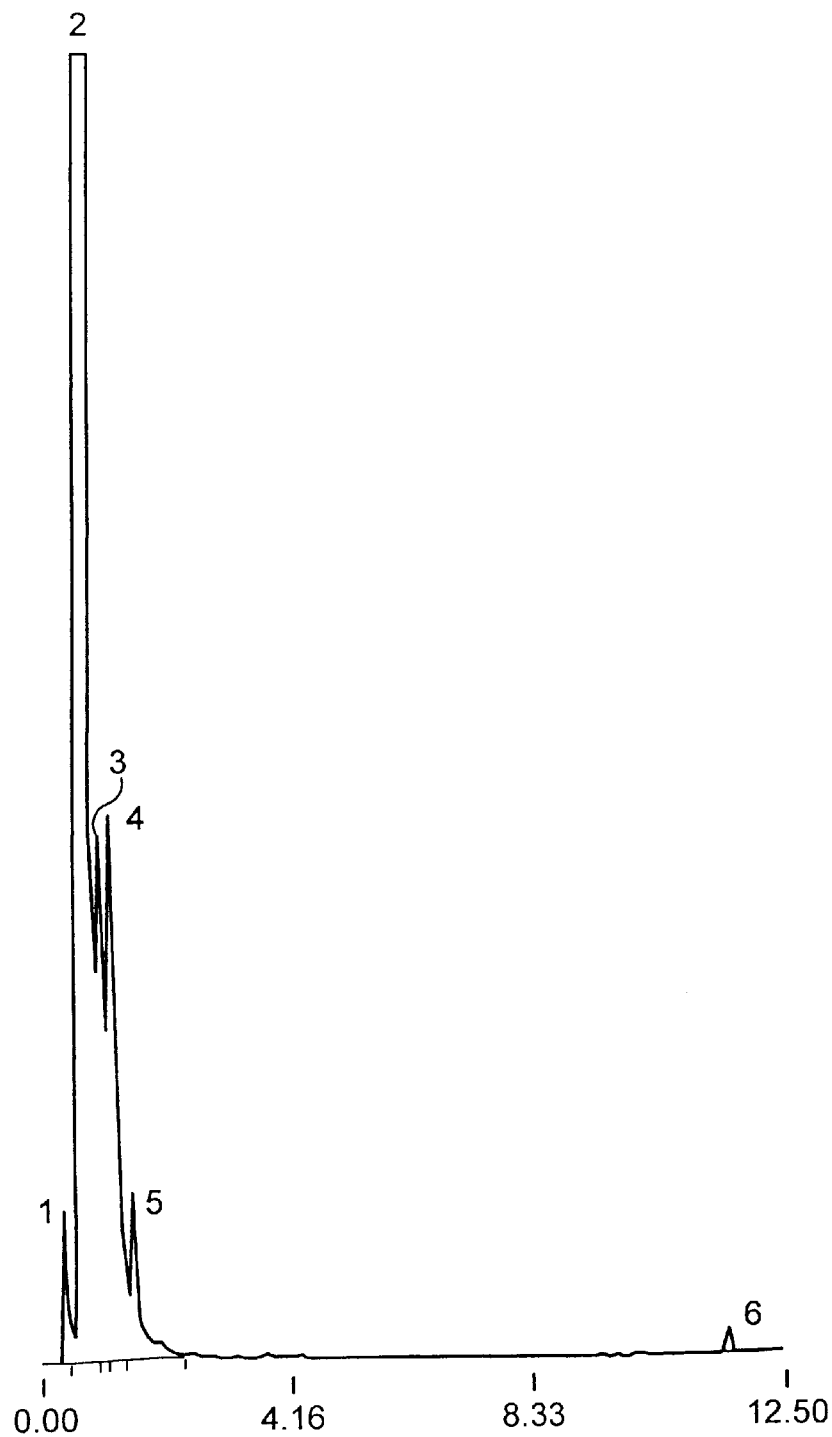
F I G. 12C: COUNTERCURRENT PURIFIED MEDIUM FROM CRUDE MEDIUM EXTRACT, NOT EXTRACTED WITH ACETONE F I G. 13A: ACETONE SUPERNATANT OF MYCOLIC ACIDS
FROM *M. TUBERCULOSIS*,
EXTRACTED WITH ACETONE AFTER
COUNTERCURRENT PURIFICATION

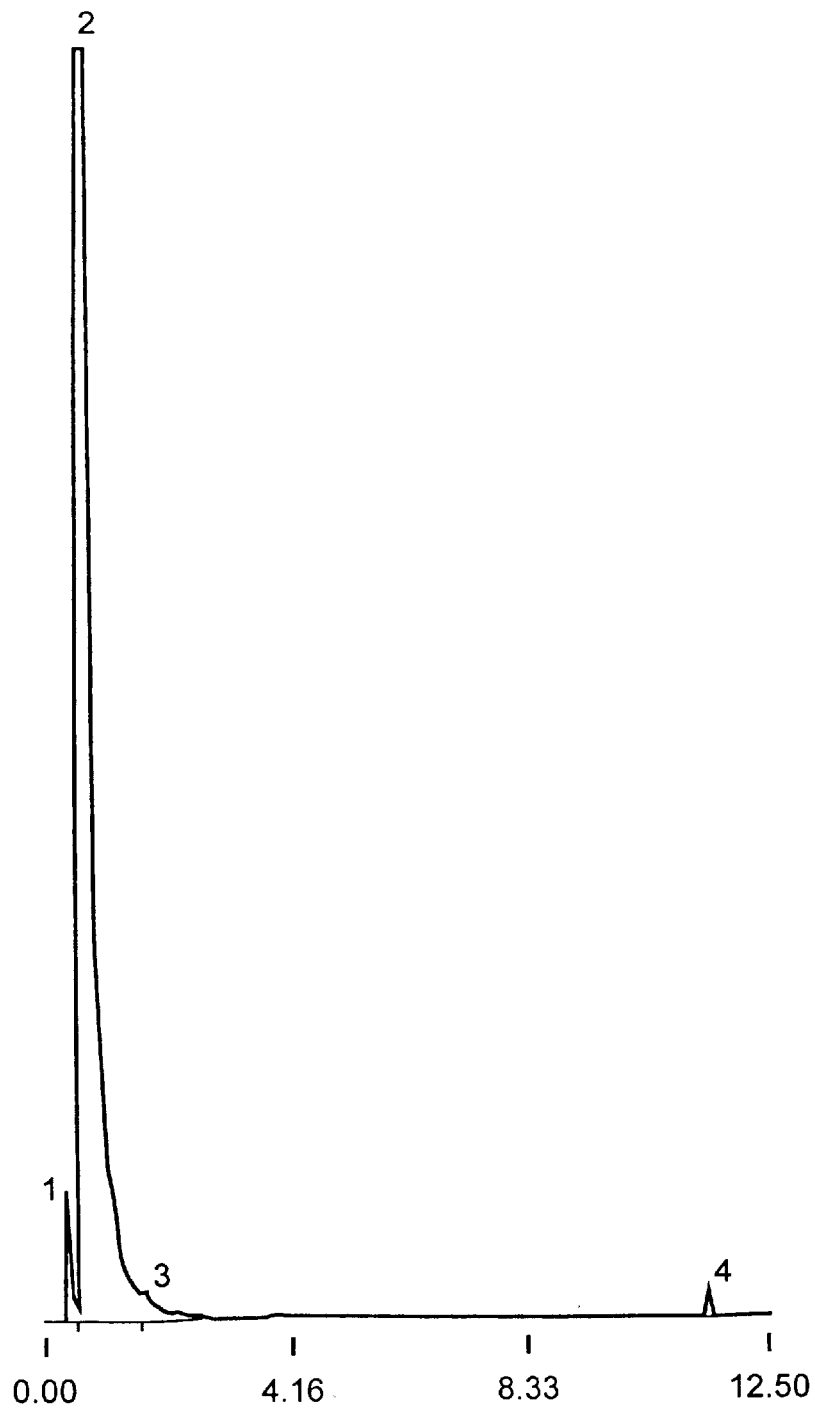
F I G. 13B: ACETONE SUPERNATANT OF REAGENTS EXTRACTED WITH ACETONE AFTER COUNTERCURRENT PURIFICATION

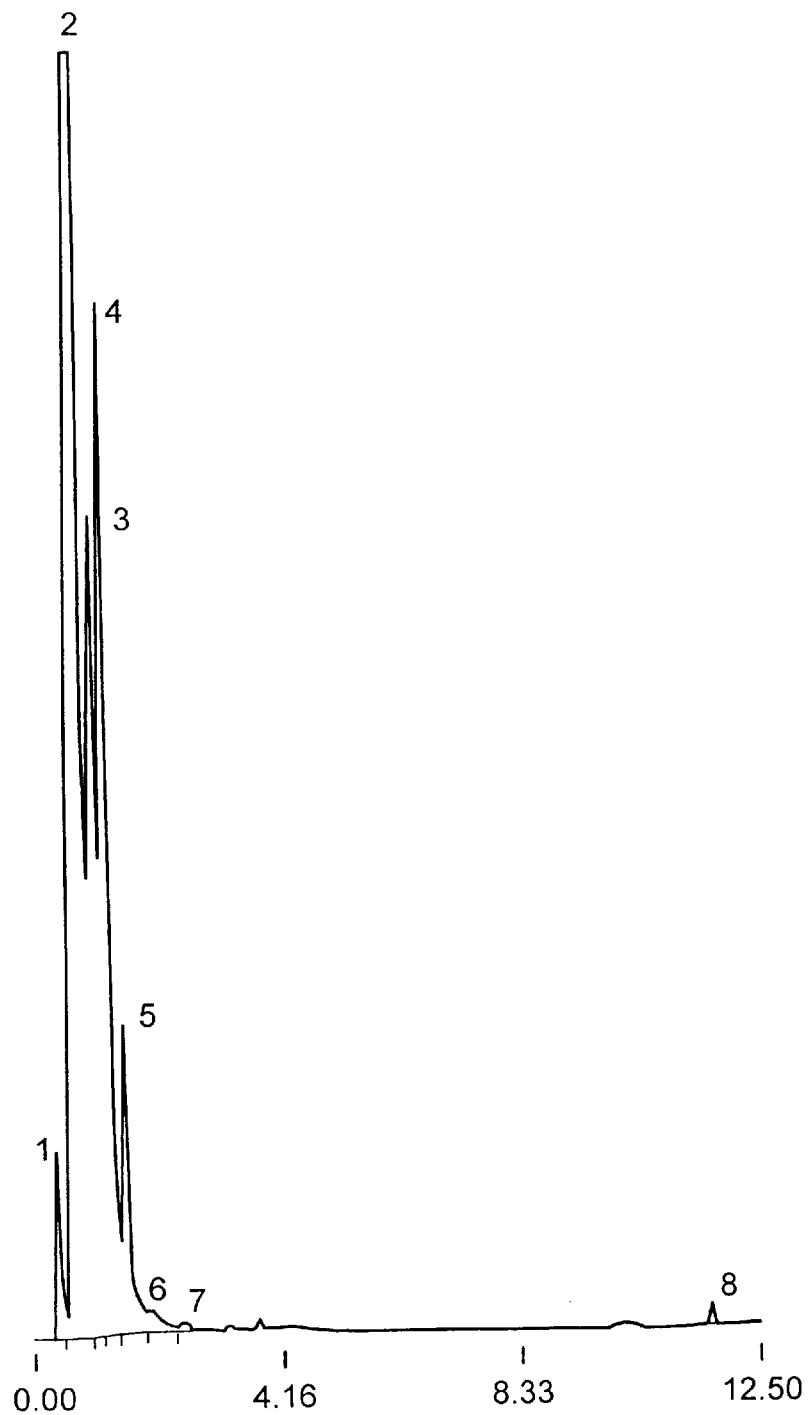
FIG. 13C: ACETONE SUPERNATANT OF MEDIUM EXTRACTED WITH ACETONE AFTER COUNTERCURRENT PURIFICATION

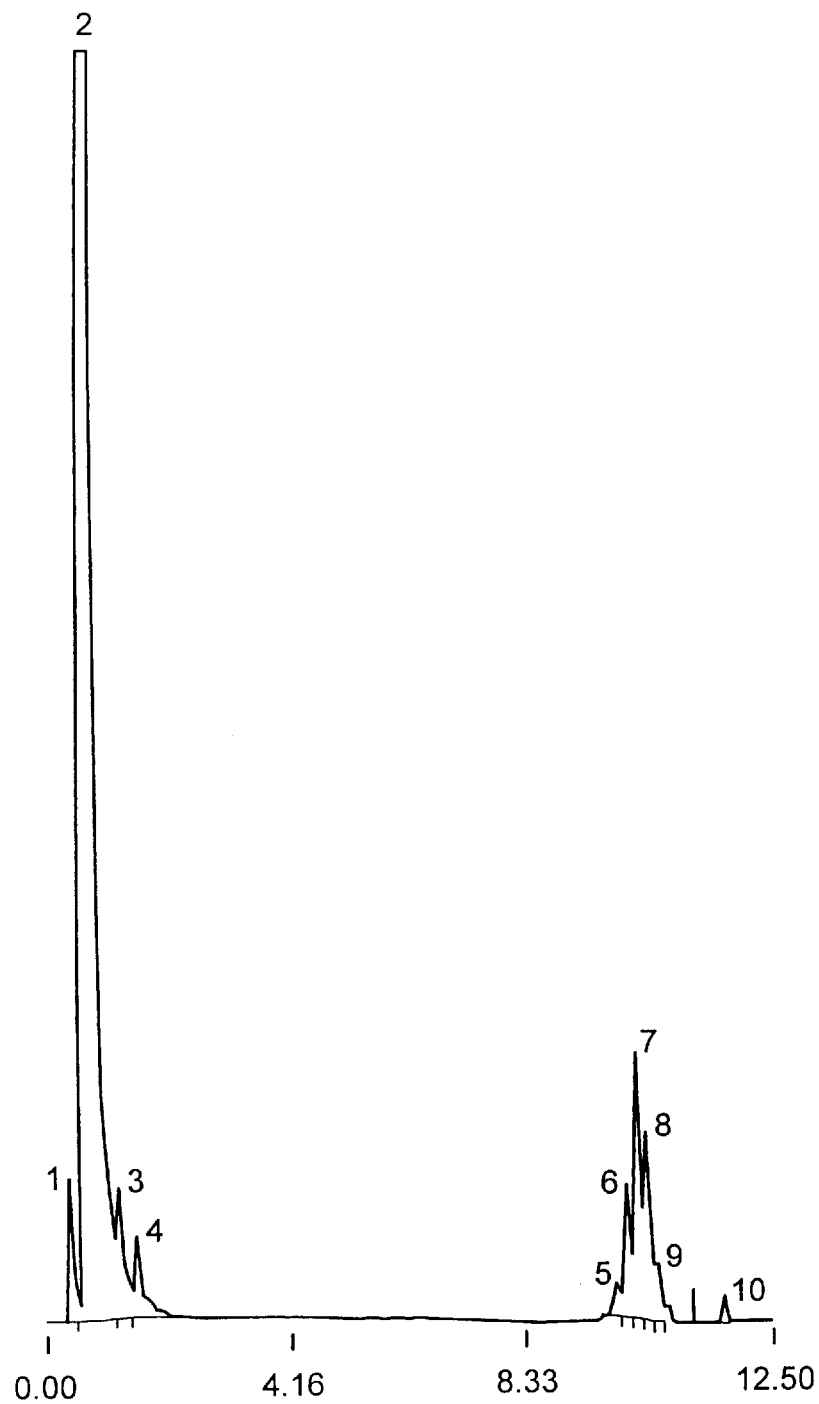
FIG. 14A: PURIFIED MYCOLIC ACIDS FROM *M. TUBERCULOSIS*, EXTRACTED W

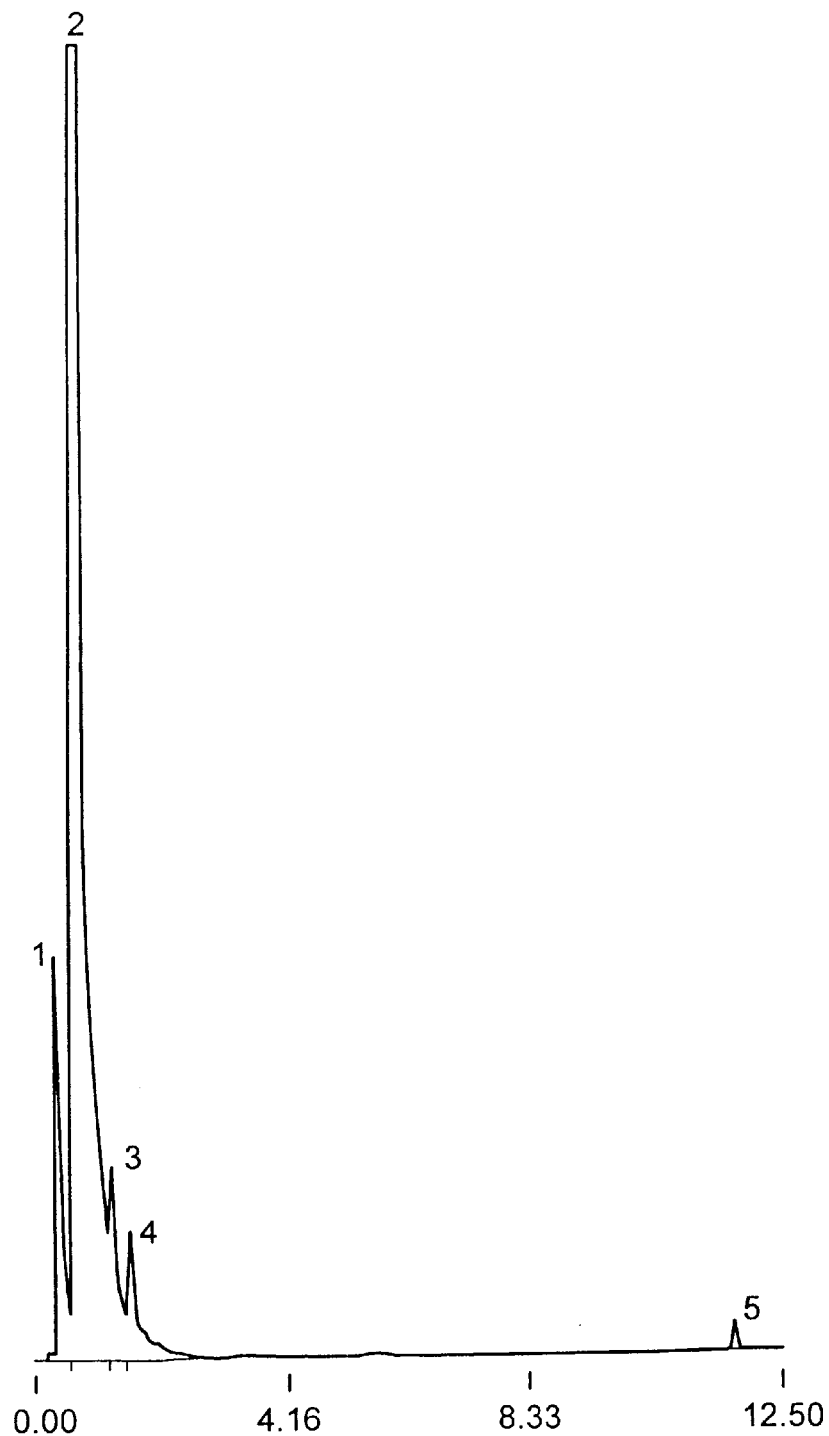
FIG. 14B: PURIFIED REAGENTS, EXTRACTED WITH ACETONE AFTER COUNTERCURRENT PURIFICATION

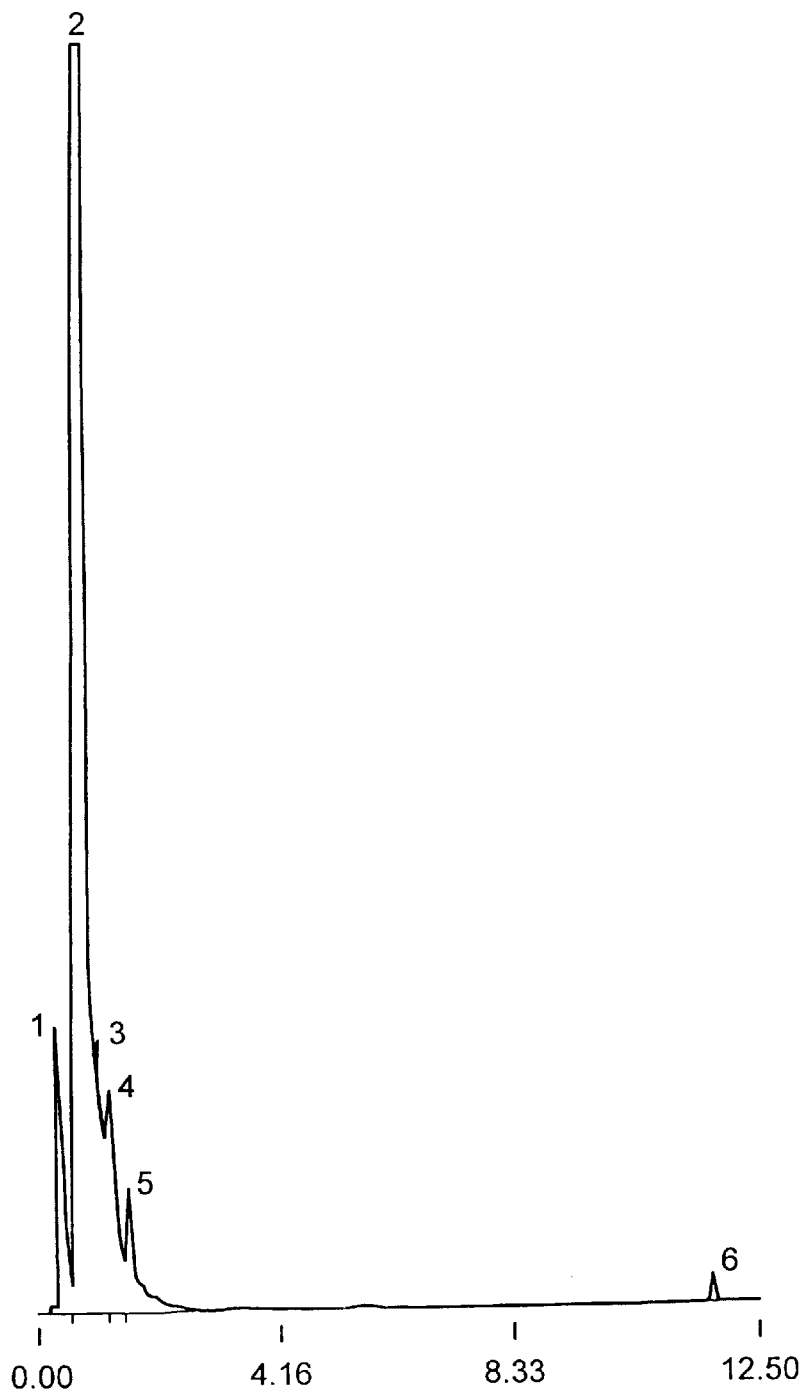
FIG. 14C: PURIFIED MEDIUM, EXTRACTED WITH ACETONE AFTER COUNTERCURRENT PURIFICATION

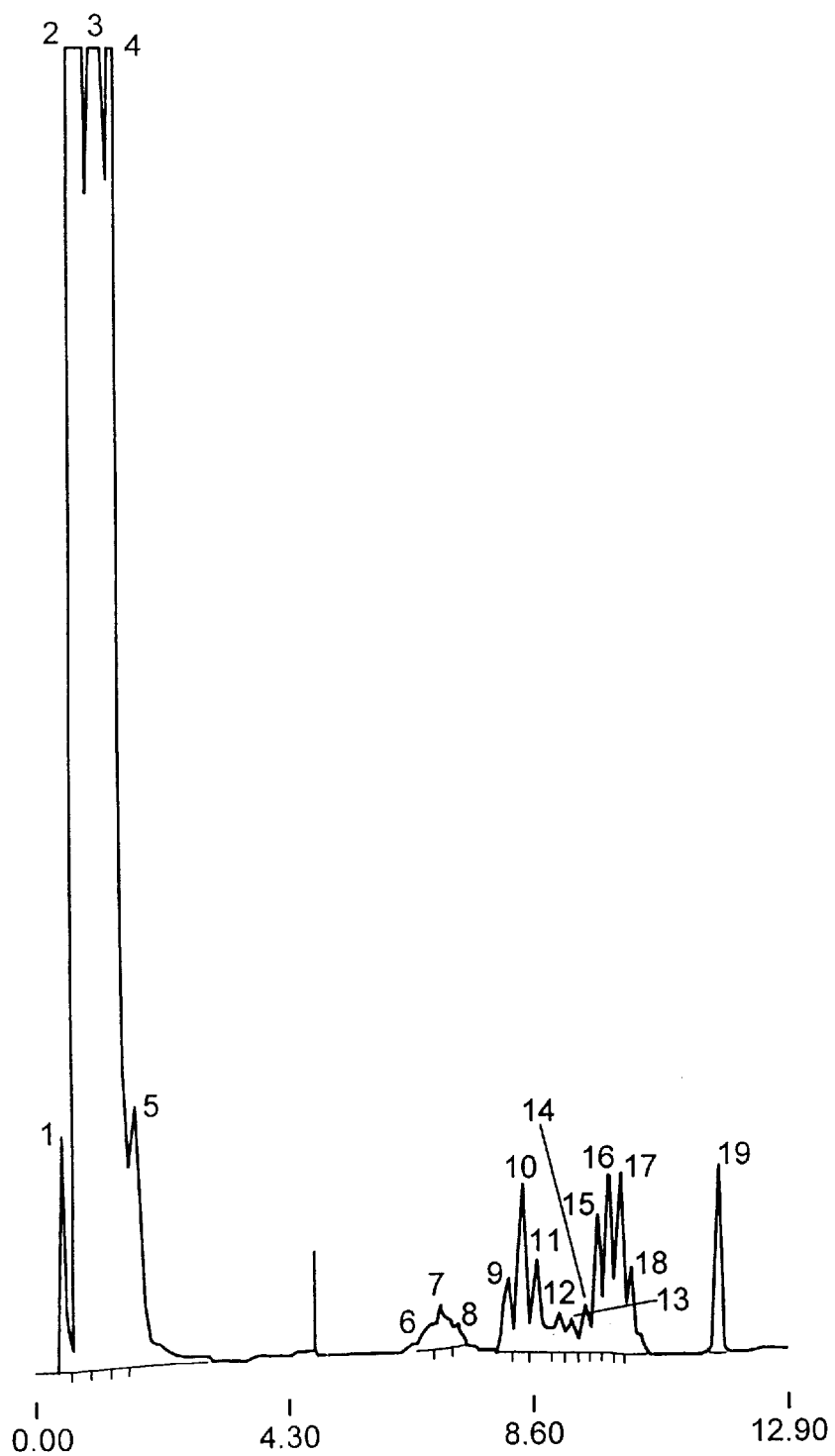
F I G. 15A: CRUDE EXTRACT FROM *M. VACCAE*, RESAPONIFIED

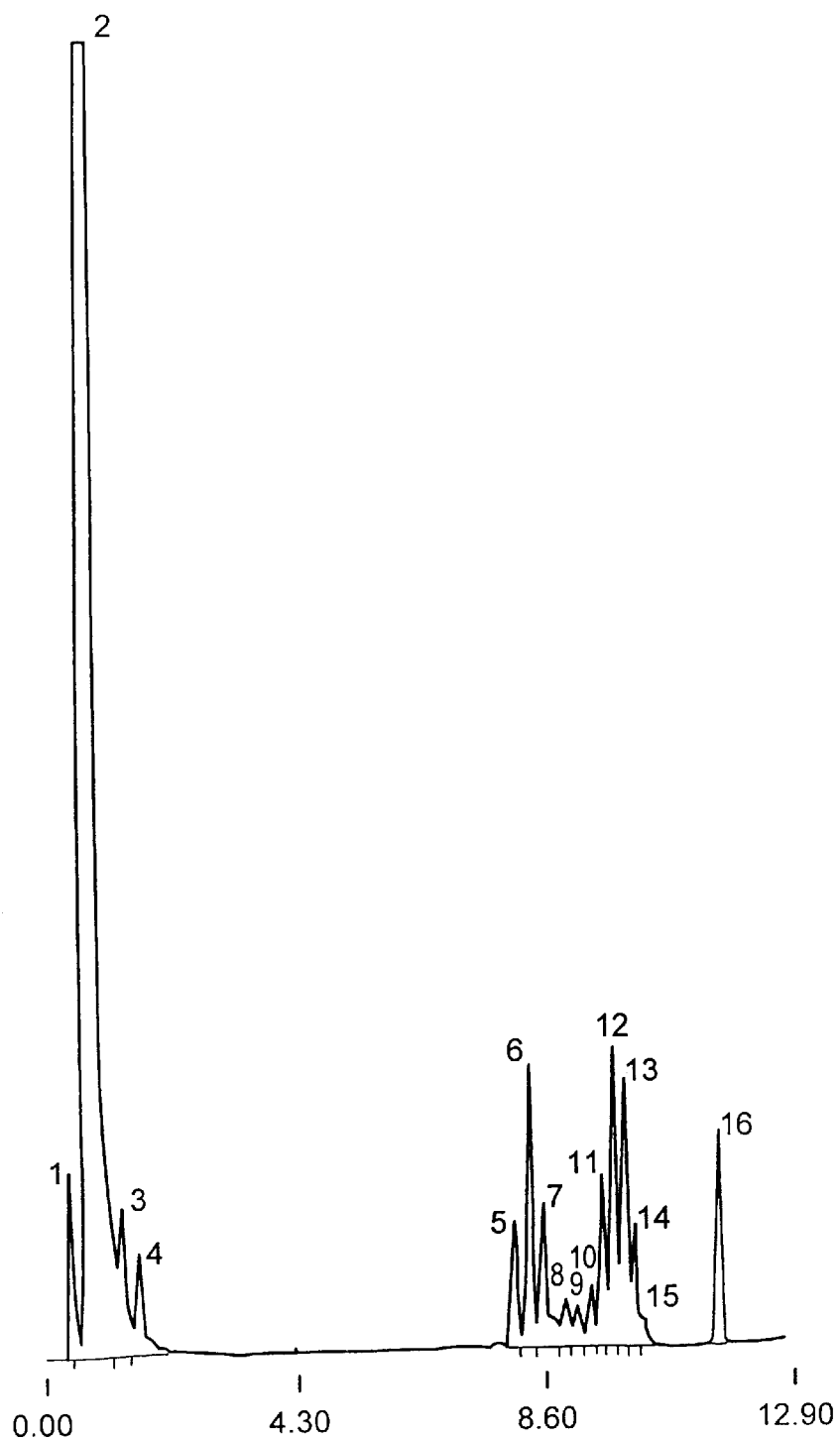
F I G. 15B: MYCOLIC ACIDS FROM *M. VACCAE*, EXTRACTED WITH ACETONE, AFTER COUNTERCURRENT PURIFICATION

METHOD FOR THE ISOLATION AND PURIFICATION OF LIPID CELL-WALL COMPONENTS

BACKGROUND OF THE INVENTION

This invention relates to the isolation and purification of lipid cell-wall components originating from bacteria assigned to the genera Mycobacterium, Corynebacterium, Nocardia or Rhodococcus, of which the most ubiquitous and the most important from a human health point of view is the genus Mycobacterium.

The genus Mycobacterium comprises a large number of both saprophytic and pathogenic species. The best known members of the genus, *M. tuberculosis* and *M. leprae,* are the causative agents of tuberculosis and leprosy, respectively, both among the most serious diseases occurring in man.

Tuberculosis: Current status

Tuberculosis is considered to be the major communicable disease throughout most of the world. Despite great advances in medical science and a range of effective drugs, which for some time created the impression that the disease had been conquered, and despite organised international efforts, tuberculosis remains a world health problem of staggering proportions: approximately one third of the world's population is infected with *M. tuberculosis* (Fauci, 1995), more than 8 million new cases world-wide and more than 3 million deaths in the year 1990 alone were reported (Snider, 1994). Predictions made by the World Health Organisation indicate that by the year 2000 the annual figures will grow to 10,2 million new cases and 3,5 million deaths, with Asia and sub-Saharan Africa being the most affected continents (De Cock et al., 1992; Dolin, Raviglione and Kochi, 1994; Raviglione, Snider and Kochi, 1995; Wilkinson and de Cock, 1996). According to the recently released "WHO Report on the Tuberculosis Epidemic, 1995" the figures anticipated for the next decade are even more alarming: 300 million new infections and 30 million deaths (Holler, 1995). In effect, tuberculosis was declared in 1993 by WHO to be a global public health emergency (Bloomfield, 1995; Wilkinson and de Cock, 1996).

The major reasons for this dramatic comeback and the unabated spread of tuberculosis can be identified as:

1) Insufficient protection offered by the world-wide vaccination programme based on the use of BCG*

*) BCG: (Bacillus of Calmette and Guerin) Calmette and Guerin attenuated a strain of *M. bovis* by passing it 231 times over a period of 13 years through a medium containing glycerine and oxbile.

2) Problems associated with the detection of tuberculosis

3) Problems associated with treatment of tuberculosis and the occurrence of multi-drug resistant strains of *M. tuberculosis*

4) Interaction with HIV infection

5) Socio-economic aspects

1. Insufficient Protection Offered By The World-Wide Vaccination Programme Based On BCG Attempts to prevent the spread of tuberculosis by inducing resistance to the infection with *M. tuberculosis* were initiated at the beginning of this century, using vaccination with BCG. On the basis of a number of controlled studies it was established that the protective efficacy obtained in vaccination with BCG varied between 0 to 80% (Snider, 1994; Hershfield, 1995) and, on the basis of the analysis of the published literature, the BCG vaccination was found to be roughly 50% effective (Colditz et al., 1994; O'Brien, 1995). A number of hypotheses/explanations for this unsatisfactory situation have been put forward (Fine, 1994). The most important are:

i) Variations between BCG vaccines, which could be caused by strains variation or by differences between manufacturing processes;

ii) Differences in pathogenesis of *M. tuberculosis;* iii) Differences in the exposure to the environmental mycobacteria—the environmental mycobacteria may act antagonistically or synergistically with BCG;

iv) Genetic differences between population groups subjected to vaccination with BCG;

v) Differences in nutrition and exposure to sunlight between various population groups;

vi) Differences between designs of various studies;

vii) Inadequacies of the criteria used for the evaluation of protective action of vaccination with BCG.

2. Problems Associated With The Detection Of Tuberculosis

The accurate and timely detection of tuberculosis and related mycobacterial diseases is one of the important requirements for the development of a more successful global strategy to combat these diseases.

Traditional laboratory detection methods have major disadvantages of either not being capable of distinguishing between live and dead bacilli (the quick and simple Ziehl-Neelsen staining) or, if these methods confirm the presence of the live bacilli (direct cultivation), a number of weeks is required before the laboratory tests are completed. This in turn, may delay the commencement of treatment and may lead to further spread of the disease.

Although recently developed molecular approaches to the diagnosis of tuberculosis (Godfrey-Faussett, 1994; Richeldi, Barnini and Saltini, 1995; Bloomfield, 1995; Vlaspolder, Singer and Roggeveen, 1995) resulted in the introduction of these rapid and sensitive detection tools by advanced laboratories in the developed countries, they are expensive and require specially trained personnel. For these reasons they are not suitable for screening/detection of tuberculosis in resource-poor, TB-endemic regions, already overburdened with the cost of controlling the disease (O'Brien, 1995; Voelker, 1995).

A similar situation exists in the field of rapid drug sensitivity testing (Schaberg et al., 1995; Pretorius et al., 1996) and rapid culturing of Mycobacterium (Bloomfield, 1995). The significant advances in these areas cannot be utilised, for financial reasons, in the countries most affected by the tuberculosis pandemic.

3. Problems Associated With Treatment Of Tuberculosis And The Occurrence Of Multi-Drug Resistant Strains Of *M. tuberculosis*

The development of effective chemotherapy for tuberculosis made the treatment of infected persons possible, thus preventing the full development of the disease. Although the anti-tuberculosis drugs with proven bacterial action (rifampicin, isoniazid and pyrazinamide) as well as the ones with bacteriostatic or resistance-preventing properties (streptomycin sulphate, ethambutol and thiacetazone) are available (Weil, 1994), worldwide success in combating the disease has not been achieved so far due to two main factors: patients' non-compliance with the prescribed regimen and financial limitations existing in developing countries.

The impact of the isoniazid preventative therapy on the control of tuberculosis in developing countries is uncertain. This approach, although widely practiced in North America, has two major disadvantages. Firstly, it may have to given for the duration of the TB sufferers' life and, secondly, its cost, i.e. US$18 per patient per 6-month course may be prohibitive, particularly in the most affected areas where an amount of US$4 per patient per year is available for total health care (O'Brien, 1995).

The interrupted and/or uncompleted treatment, apart from the detrimental effects on the individual concerned, has contributed to the emergence and spread of multi-drug resistant strains of *M. tuberculosis,* which further complicate the overall situation (Beyers et al., 1996). The recent WHO estimates indicate that 50 million people worldwide may already be carrying strains of *M. tuberculosis* resistant to one or more of the most common anti-TB drugs. It was established already in 1991, that one third of all TB patients in New York were resistant to at least one drug and almost 20% were resistant to rifampicin and isoniazid combined (Henderson 1995).

4. Interaction With HIV Infection

The close association documented between tuberculosis and HIV infection as well as the frequently concomitant presence of both these diseases add gravity to the situation (Torres et al., 1990; De Cock, 1994; Cantwell and Binkin, 1994; Murray, 1994; Antonucci et al.. 1995; Mofeson et al., 1995; Davies, Wilkinson and Colvin, 1996; Wilkinson and Moore, 1996). The number of people who develop tuberculosis in Asia because of the parallel infection with the HIV is expected to increase seven-fold this decade, according to the Public Health Reports (1995).

The emergence of multiple-drug resistance among the strains of *M. tuberculosis* and other atypical mycobacteria has introduced an additional dimension to this problem (Blumberg, Miller and Koornhof, 1994; Morse, 1994; Yew and Chau, 1995).

5. Socio-Economic Aspects

Other reasons contributing to a further spread of the disease, such as unemployment, overcrowding, general lowering of economic conditions, alcoholism and erosion of the public health infrastructure have been recently reviewed by Darbyshire (1995), Fauci (1995), Law et al., (1995) and Mangtani et al., (1995).

The increased influx of immigrants from the endemic areas to countries where tuberculosis has been well under control, e.g. United States of America, creates additional problems in containing the spread of tuberculosis (Huebner and Castro, 1995). The incidence of tuberculosis among immigrants to the USA is reported to be 12 times higher than that observed among the native-born population (Ballew and Becker, 1995).

The trends discussed above place an overwhelming pressure on the improvement of existing approaches to case-management of TB patients both in endemic areas and developing countries and on the development of new drugs capable of preventing and/or combating tuberculosis (Cole, 1995; Voelker, 1995). Although cautious optimism can be detected among the researchers involved in both fields (Mwinga, 1995; Grosset, 1995), currently prevailing economic restrictions, even in the developed countries, place serious limitations on funding required to develop new anti-tuberculosis drugs, the cost of which is estimated at US$150 million for each new compound (Grosset, 1995).

Immunological Prospects For Prevention And Treatment

In view of the seriousness of the problems listed above, the limitations associated with the existing methods of combating tuberculosis and the high costs of developing new forms of chemoprophylaxis and chemotherapy, immunological approaches could provide a relevant and realistic alternative to finding an effective and economically affordable solution to the control and treatment of tuberculosis and associated conditions.

Results obtained from a number of trials using treatment with killed cells of *M. vaccae* (Stanford and Grange, 1994) suggest that this saprophytic microorganism may find application in immunotherapy of tuberculosis either as a single agent (Bahr et al., 1990a; Bahr et al., 1990b; Stanford et al., 1990a) or in conjunction with chemotherapy (Stanford et al., 1990b; Prior et al., 1995; Onybebujoh et al., 1995).

The modulation of inflammatory processes attributed to the use of thalidomide has recently been utilised in combating tuberculosis. The beneficial effects of thalidomide on the clinical manifestation of tuberculosis reported by Cole (1995) provide grounds for considering the immunomodulatory properties of this drug in the treatment of the disease. These effects of thalidomide are attributed to its potent inhibitory action on tumour necrotic factor, a cytokine involved in the inflammatory processes accompanying tuberculosis.

The advantages stemming from these two approaches may be extended to treatment of drug-resistant forms of tuberculosis. Encouraging data have been reported in this respect from a number of trials undertaken in Iran (Etemadi, Farid and Stanford, 1992) and in Kuwait, Rumania, Vietnam and India (Stanford and Grange, 1993).

Immunological Targets

Attempts at identification of immunologically active components of *M. tuberculosis* over the last decades focused mainly on proteins (Daniel, 1984; Chaparas, 1984; Yanez et al., 1986; Deshpande et al., 1994; Torres et al., 1994), polysaccharides (Daniel, 1984; Misaki, Azuma and Yamamura, 1987), peptidoglycolipids and phospholipids (Brennan, 1984), lipopolysaccharides (Hunter, Gaylord and Brennan, 1986), glycolipids (Brennan, 1984; Mc Neil et al., 1989) and lipoarabinomannan (Arya, 1993; Sieling et al., 1995).

Although lipid cell-wall components have been associated with the virulence of *M. tuberculosis* (Collins, 1994), these compounds, being of lipid nature, i.e. β-hydroxy fatty acids, have been considered not to possess immunogenic properties. The possibility that mycolic acids might play a significant role in the complex process of immunological response/s of the human body to the infection with *M. tuberculosis* has become apparent only recently.

A humoral response to a mycolic acids-BSA conjugate was first observed in 1994 (South Africa Patent Application No 95/3077 and PCT Patent Application No. WO 95/28642). At about the same time, a measurable cellular immune response to mycolic acids was demonstrated by Beckman et al., (1994). The authors discovered that these compounds stimulated proliferation of a rare subset of human double-negative T-cells and described a new way of antigen presentation by CD1 molecules occurring on professional antigen-presenting cells like macrophages and dendritic cells (Beckman et al., 1994; Beckman et al., 1995; Rosat et al., 1995). Likewise, prenyl pyrophosphate was also found to be presented by CD1 molecules on antigen-presenting cells (Morita et al., 1995).

Lipid Cell-Well Components of Mycobacteria

The mycobacterial cell wall is considered to be a highly differentiated and complex structure, characterised by a very high content of lipids, which constitute about 60% of the cell wall mass (Grange, 1988). Its diagrammatic presentation is given in FIG. 1.

Mycolic acids, the major lipids of the cell wall of Mycobacteria (Petit and Lederer, 1984), are considered to be a major component of an outer permeability barrier (Wheeler et al., 1994) and are responsible for the "acid-fastness" of this group of microorganisms (Grange, 1988). The presence of large amounts of mycolic acids associated with different types of free lipids constitutes the basis of the integrity of the mycobacterial wall (Besra et al., 1993).

Mycolic acids occur in nature as mixtures of different types. They frequently form esters with carbohydrates, e.g. with arabinose forming the main cell wall palisade and with trehalose forming dimycolyl trehalose, the so called cord factor which is associated with the virulence of *M. tuberculosis*. Mycolic acids have been reported in bacterial species other than Mycobacterium, i.e. in Corynebacterium and Nocardia (Goren, 1972). Consequently, three major categories of mycolic acids are distinguished (The Merck Index, 1989), namely:

i) corynomycolic acids ($C_{28}$–$C_{40}$ acyl chain length)
ii) nocardomycolic acids ($C_{40}$–$C_{60}$ acyl chain length)
iii) mycobacterial mycolic acids ($C_{60}$–$C_{90}$ acyl chain length).

Mycolic acids are high molecular weight β-hydroxy fatty acids which have moderately long aliphatic chains at the α-position. The general formula of these compounds is shown in FIG. 2.

All known mycolic acids have the basic structure $R^2CH(OH)CHR^1COOH$, where $R^1$ is a $C_{20}$ to $C_{24}$ linear alkane and $R^2$ is a more complex structure of 30 to 60 carbon atoms that may contain various numbers of carbon-carbon double bonds and/or cyclopropane rings, methyl branches or oxygen functions such as C=O, $CH_3OCH=$,COOH (The Merck Index, 1989). Although there exists a great variety of mycolic acids, the α branch, except for length, is essentially invariant/constant in any group of mycolic acids (Goren, 1972).

Mycolic acids are soluble in a very limited range of solvents, which complicates their purification (Brennan and Nikaido, 1995) and leads to tedious and costly protocols. Beckman et al., (1994), for example, achieved purification of mycolic acids from *M. tuberculosis* only after derivatization with para-bromophenacylbromide, reversed phase HPLC separation, collection of the mycolic acids peak cluster fraction, resaponification and extraction.

Anticipating the potential role which lipid cell-wall components, and in particular mycolic acids, can play in immunotherapy and immunoprevention of tuberculosis and/or its side effects, a new, more efficient method of purifying large quantities of these components is described in this invention.

SUMMARY OF THE INVENTION

According to the invention a method of separating and purifying a specific microbial cell-wall component of a lipid or sugar nature or a derivative or analog thereof from an extracted mixture of the cell-wall component or derivative or analog thereof and contaminants or from a synthetic mixture of the cell-wall component or derivative or analog thereof and contaminants comprising the steps of:

dissolving the extracted mixture or synthetic mixture in a bi-phasic solvent to form a solution;

allowing the solution to separate to form an upper phase and a lower phase;

subjecting the phases to countercurrent distribution (CCD) separation comprising a required number of cycles to separate the microbial cell-wall component or analog or derivative thereof in the upper phase or the lower phase; and removing the separated microbial cell-wall component or derivative or analog thereof from the upper or lower phase.

The specific cell-wall component or derivative or analogue thereof may be a lipid or a sugar.

The specific cell-wall component or analogue or derivative thereof is preferably a lipid.

More preferably, the lipid is a fatty acid.

More preferably, the lipid is a mycolic acid.

More preferably still, the cell-wall component is a group of components or analogues or derivatives thereof and the group is a mixture of mycolic acids or derivatives or analogues thereof.

The microbial cell-wall component may be derived from a bacterium, a fungus or a yeast.

The microbial cell-wall component is preferably derived from a bacterium which may be selected from Mycobacteria, Corynebacteria, Nocardia, Rhodococci, Amycolata and other suitable bacterial species.

When the bacterium is selected from Mycobacteria, it may be selected from the strains of *M tuberculosis, M. avium* and M. vaccae.

The bi-phasic solvent system preferably comprises chloroform, methanol and water.

The bi-phasic solvent system preferably comprises an upper liquid phase and a lower liquid phase.

The method preferably also comprises the steps of mixing and equilibrating the upper and lower phases of the solvent system.

Preferably, the composition of the upper phase is 12–18% chloroform, 45–55% methanol and 25–40% water. More preferably, the composition of the upper phase is 15% chloroform, 52% methanol and 33% water.

Preferably, the composition of the lower phase is 50–80% chloroform, 15–40% methanol and 2–8% water. More preferably, the composition of the lower phase is 68% chloroform, 27% methanol and 5% water.

The liquid-liquid phase extraction may be a countercurrent extraction or a multiple extraction of one of the phases.

The purified cell-wall component or analogue or derivative thereof may be subjected to an acetone extraction to remove impurities.

Preferably, the cell-wall component or analogue or derivative thereof needs no chemical derivatisation to separate it from any impurities which may arise from microbial growth, microbial-growth media or the synthetic mixture.

The purified cell-wall component or derivative or analogue thereof may be saponified to reverse any methyl esterification thereof.

BRIEF DESCRIPTION OF THE DRAWINGS

The invention will now be described in more detail, by way of example only, with reference to the accompanying drawings in which:

FIG. 8A is a graph showing an HPLC of a crude *M. tuberculosis* extract;

FIG. 8B is a graph showing an HPLC of a crude reagents extract;

FIG. 8C is a graph showing an HPLC of a crude medium extract;

FIG. 9A is a graph showing an HPLC of an acetone extracted supernatant of the crude *M. tuberculosis* extract;

FIG. 9B is a graph showing an HPLC of an acetone extracted supernatant of the crude reagents extract;

FIG. 9C is a graph showing an HPLC of an acetone extracted supernatant of the crude medium extract;

Figure 10A:
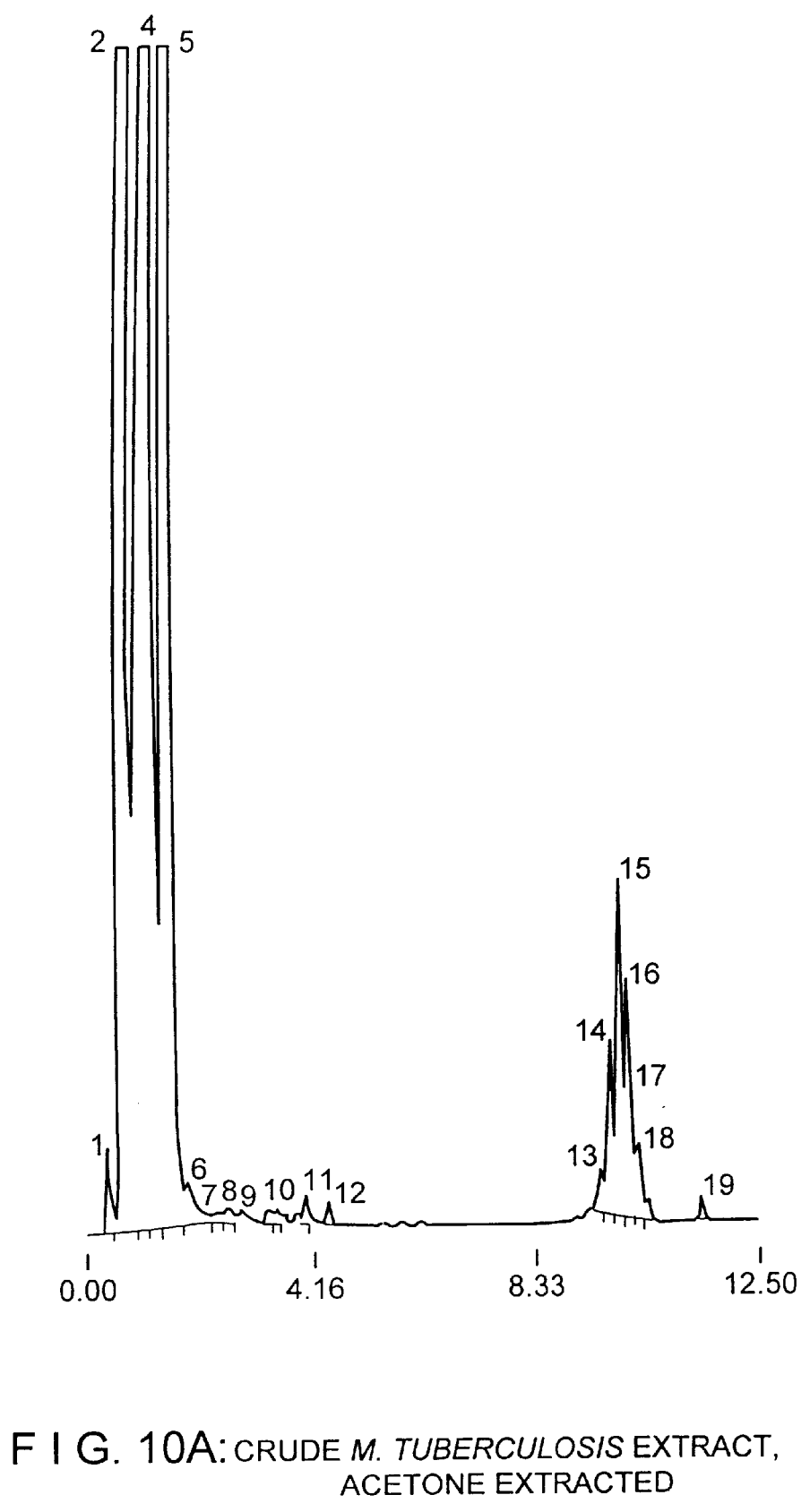

FIG. 10A is a graph showing an HPLC of a crude *M. tuberculosis* extract, acetone extracted;

FIG. 10B is a graph showing an HPLC of a crude reagents extract, acetone extracted;

FIG. 10C is a graph showing an HPLC of a crude medium extract, acetone extracted;

FIG. 11A is a graph showing an HPLC of countercurrent purified mycolic acids of *M. tuberculosis,* from acetone extracted crude extract;

FIG. 11B is a graph showing an HPLC of countercurrent purified reagents from acetone extracted crude extract;

FIG. 11C is a graph showing an HPLC of countercurrent purified medium from acetone extracted crude extract;

FIG. 12A is a graph showing an HPLC of countercurrent purified mycolic acids from a crude extract of *M. tuberculosis,* not extracted with acetone;

FIG. 12B is a graph showing an HPLC of countercurrent purified reagents from crude reagent extract, not extracted with acetone;

FIG. 12C is a graph showing an HPLC of a countercurrent purified medium from crude medium extract, not extracted with acetone;

FIG. 13A is a graph showing an HPLC of an acetone supernatant of mycolic acids from *M. tuberculosis,* extracted with acetone after countercurrent purification;

FIG. 13B is a graph showing an HPLC of an acetone suprernatant of reagents extracted with acetone after countercurrent purification;

FIG. 13C is a graph showing an HPLC of an acetone supernatant of medium extracted with acetone after countercurrent purification;

FIG. 14A is a graph showing an HPLC of purified mycolic acids from *M. tuberculosis,* extracted with acetone after countercurrent purification;

FIG. 14B is a graph showing an HPLC of purified reagents, extracted with acetone after countercurrent purification;

FIG. 14C is a graph showing an HPLC of a purified medium, extracted with acetone after countercurrent purification;

FIG. 15A is a graph showing an HPLC of a crude extract from *M. vaccae,* resaponified; and FIG. 15B is a graph showing an HPLC of mycolic acids from *M. vaccae,* rinsed with acetone, after countercurrent purification.

Figure 1:
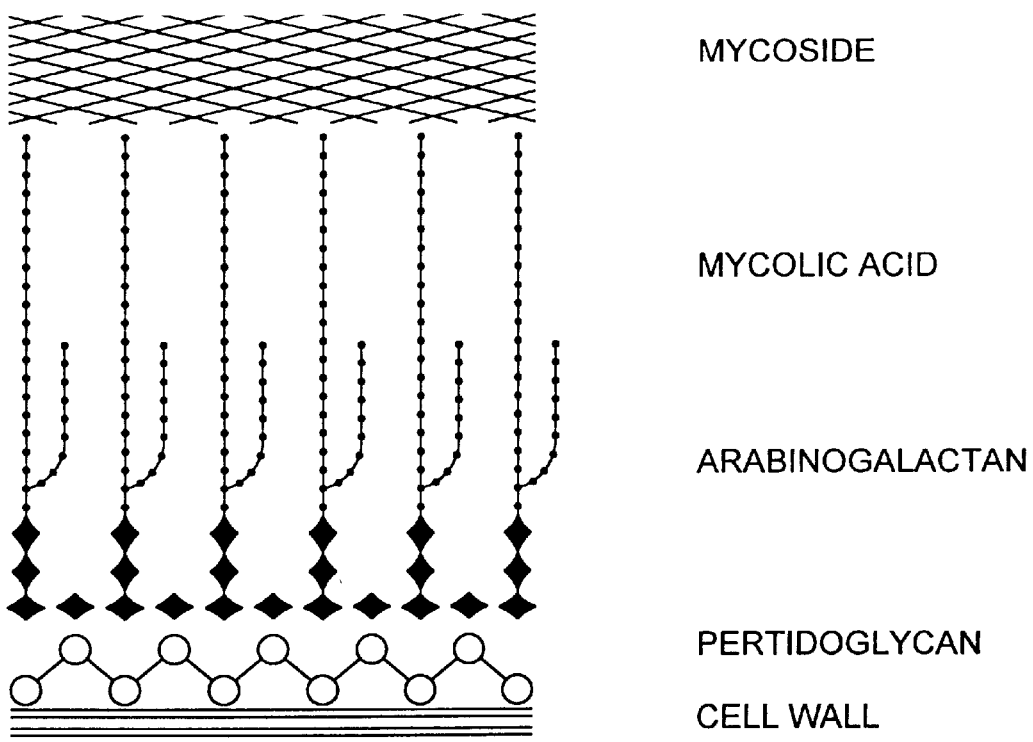
FIG. 1 is a diagrammatic representation of a mycobacterial cell wall.
Figure 2:
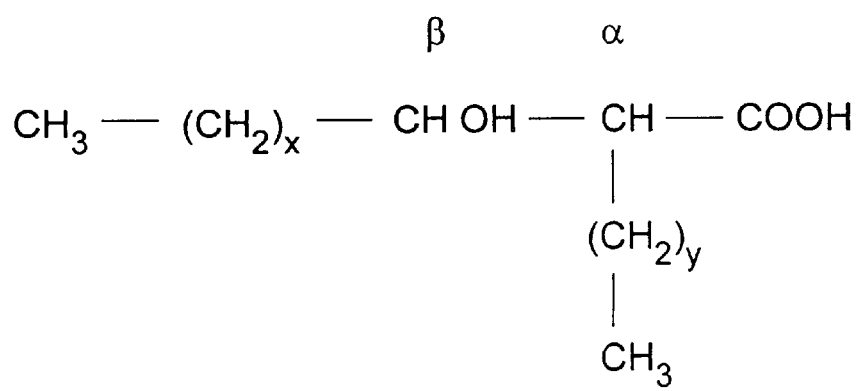
FIG. 2 is the general formula of mycolic acids.
Figure 3:
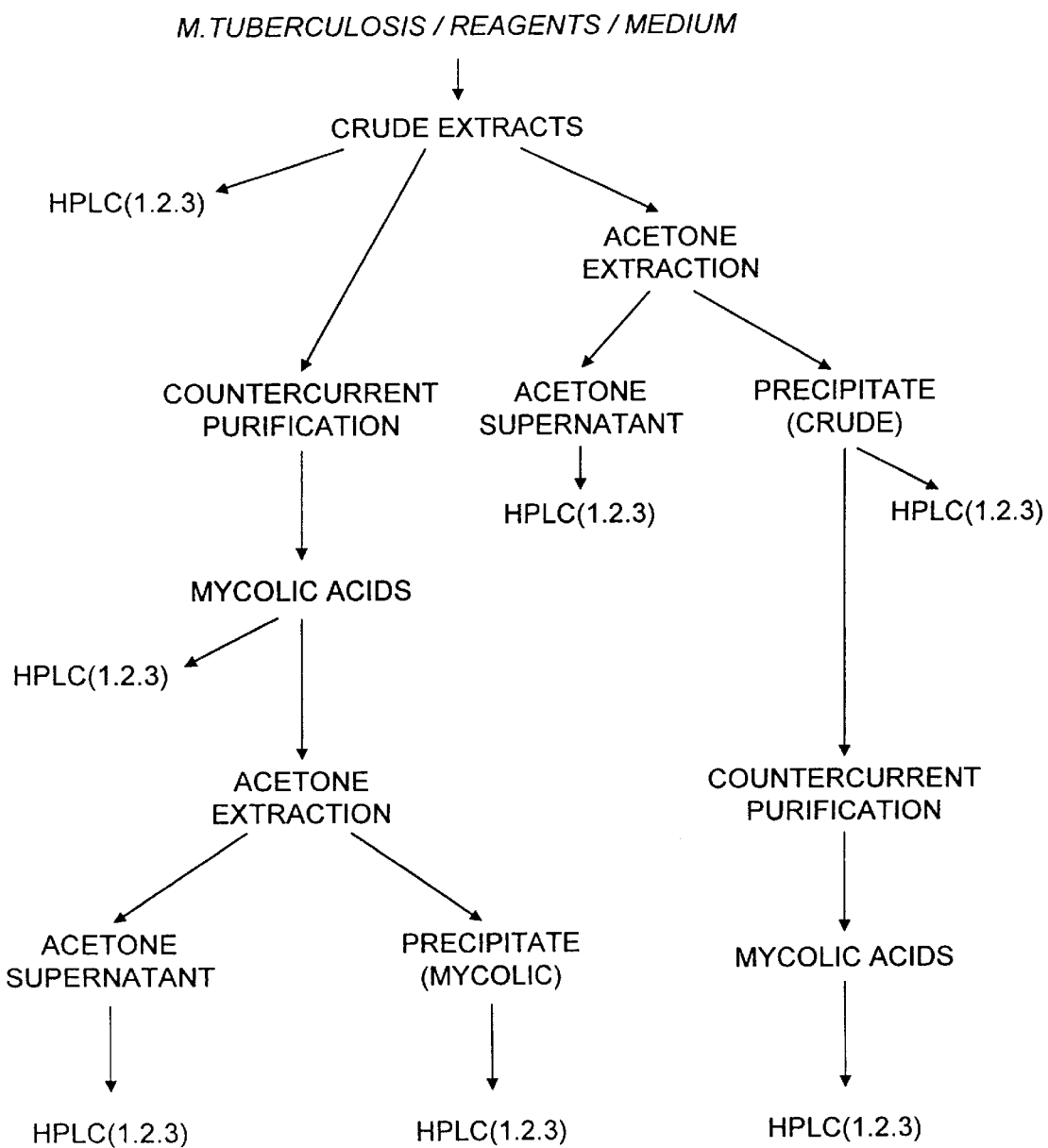
FIG. 3 is a flow chart showing a procedure for purification of mycolic acids from a crude lipid cell-wall extract originating from *M. tuberculosis;*

A schematic representation of the various purification procedures performed on crude extracts of bacterial cell-wall components and the various stages at which HPLC/s were performed is set out in FIG. 3.

DESCRIPTION OF PREFERRED EMBODIMENTS

The Aim of the Invention

The aim of the present invention is to isolate microbial lipid cell-wall components and derivatives and analogues thereof, particularly mycolic acids originating from various microbial strains, to be used in:

1. The development of anti-tuberculosis and other anti-mycobacterial immunoprophylactic preparations, such as vaccines, for human and veterinary use. Such preparations can be based on mycolic acids with or without the concomitant presence of other mycobacterial cellular components and may or may not require the use of adjuvants of various types, including interleukines. The development of such preparations will include any manipulation necessary to render mycolic acids or other cell-wall lipid components immunogenic (e.g. the preparation of immunogenic conjugates, subunit vaccines).

2. The development and production of diagnostic tests for the confirmation of the presence of mycobacterial cells in samples such as sputum, cerebrospinal fluid, blood, urine, stools etc.

3. The production and commercialisation of individual purified cell-wall components, for research or other purposes (e.g. to be used as standards or for the development of diagnostic tests).

4. The immunotherapy of illness of mycobacterial and other origin, including autoimmune side effects.

5. The immunotherapy of multi-drug resistant mycobacterial infections.

6. The development of a test (in vitro or in vivo) for determining the reaction of the humoral or cellular immune system (the degree of stimulation of humoral or cellular immune system) to either the immunization or infection process.

7. The development of novel anti-tuberculosis drugs, aimed at the inhibition of the cell-wall synthesis.

8. The immune control of neoplastic disorders.

A high degree of purity of mycolic acids is important for the development of immunoprophylactic preparations, such as vaccines, immunotherapy and/or for detection methods, and more specifically for:

i) the determination of the solvent system in which the preparation of conjugates is to take place;

ii) the preparation of the conjugates necessary for the immunization of the experimental animals;

iii) the determination of the efficiency of coupling of mycolic acids to carrier molecules, i.e. for the monitoring of the conjugation process;

iv) the preparation of other conjugates required for monitoring of the process of immunization and for the development of an ELISA type immunoassay;

v) the assessment of the specificity of the produced antibodies and for their characterization;

vi) the development of novel anti-tuberculosis drugs, aimed at the inhibition of the bacterial cell-wall synthesis.

The present invention provides a method, using a bi-phasic solvent system for the simultaneous purification and separation of different classes of compounds, which may be cell-wall components or derivatives or analogues thereof which may be extracted from a culture of the relevant cells or which may be synthesized. In a prepared embodiment of the invention lipid cell-wall components of microbial origin can be separated from contaminating material and separated as a group from contaminants. Purified lipid cell-wall components, e.g. mycolic acids, as well as other lipid cell-wall components originating from bacterial cell walls of microorganisms such as Mycobacteria, Corynebacteria, Nocardia and Rhodococci, can be separated as a group by this method. Although the method is applicable to all Mycobacteria, Corynebacteria, Nocardia and Rhodococcus strains, the examples present the experimental details concerning two Mycobacteria strains.

In essence the method involves subjecting a crude extract of microbial cell-wall components, dissolved in a unique bi-phasic solvent system, to a countercurrent liquid/liquid separation to purify a specific cell-wall component on a large scale. In the case of mycolic acids, the method yields in the order of 3 to 12% of the dry weight of the crude cellular extract, of purified mycolic acid.

The method involves harvesting a growth of bacterial, e.g. mycobacterial, cells followed by saponification and extraction of lipid cell-wall components. The saponification step is necessary to release the lipid component from the rest of the cell skeleton or to release the free fatty acid salt from any ester form thereof, and the extraction step is necessary to remove the saponification agents from the cell wall component/reagent mixture.

The crude cellular extract obtained from the large-scale extraction process is dissolved in the lower phase of the bi-phasic solvent system and an amount of the upper phase of the bi-phasic solvent system is added. This solution is then subjected to countercurrent distribution through a series of approximately 25 cycles, each cycle comprises a mixing of upper and lower phases, a separation of the phases and a transfer of the separated phases to clean upper and lower phases.

Methyl esterification of the purified lipid cell-wall components occurs when they remain in methanol-containing solvents for extended periods. This is readily reversed by saponification, i.e. adding Reagent A at room temperature and re-extracting as described in the Methods.

The various groups of fatty acids from the cell-wall can be identified in the various tubes by their emulsification patterns in the lower or upper phase. The mycolic acids fraction, for example, was easily recognised by its emulsification pattern mainly in the lower phase within the first few tubes. The countercurrent-separated material is then withdrawn from the tubes. The mycolic acids fraction, even after being purified by countercurrent distribution, was still found to contain some contaminating material. An amount of acetone was added to the purified sample and this was found to extract these impurities. (It was found that if acetone was added to the crude extract, some but not all of the impurities, which could stem from the ingredients of the bacterial culture medium, were extracted.) The purified mycolic acids were subjected to HPLC analysis to determine their purity, profile and yield.

The method of the invention was applied to the purification of mycolic acids from M. tuberculosis, M. avium and M. vaccae and proved to be effective for all of these strains of mycobacteria. Thus, using the method of the invention, it has been possible for the first time to separate a relatively large quantity of mycolic acids or other specific lipid cell-wall components and to purify them for subsequent use, such as in any one of the applications listed above.

EXAMPLES

Materials

Cultures

Mycobacterium tuberculosis H37Rv ATCC 27294—a virulent strain, originally isolated from an infected human lung, was used in the experiments.

Mycobacterium vaccae ATCC 15483—a strain originally isolated from cow's milk.

The cultures were purchased in lyophilized form from the American Type Culture Collection (ATCC), Maryland, USA.

Media

The following media were used for the cultivation of M. tuberculosis and M. vaccae:

Liquid medium: Dubos broth

Solid media: Löwenstein-Jensen (LJ) medium Middlebrook 7H-10 medium

The media were prepared as recommended by Kent and Kubica (1985) in a Guide for the Level III Laboratory, Public Health U.S. Department of Health and Human Services, Atlanta.

Reagents

The following reagents were used in the purification of the extracted mycolic acids:

Chloroform (Saarchem, Analytical grade)

Methanol (Merck, Chemically pure)

Acetone (BDH, Analytical grade).

For the preparation of the reagents used for the extraction, derivatization and High-Performance Liquid Chromatography (HPLC) analysis of mycolic acids, HPLC Grade methanol and double-distilled deionized water were used.

Reagent A: 25% potassium hydroxide (Analytical Grade) dissolved in methanol-water (1:1): 62,5 g potassium hydroxide was dissolved in 125 ml water and 125 ml methanol (BDH, HPLC Grade) was added.

Reagent B: Concentrated hydrochloric acid (BDH, Analytical Grade) diluted 1:1 with water.

Reagent C: 2% potassium bicarbonate (BDH, Analytical Grade) dissolved in methanol-water (1:1): 10 g potassium bicarbonate was dissolved in 250 ml water and 250 ml methanol was added.

Reagent D: para-bromophenacylbromide in Crown Ether (Pierce Chemical Co, Cat. No 48891) was dispensed in 50 $\mu$l quantities into small amber-coloured screw cap vials with Teflon-coated septa. The caps were tightened and the vials were wrapped with Parafilm. Reagent D was stored at 4° C.

Reagent E: Reagent E was prepared by mixing reagent B 1:1 with methanol.

HPLC Standard

High Molecular Weight Internal Standard (C-100) from Ribi ImmunoChem Research Company, Cat No R-50. The standard, 1 mg, was suspended in 2,0 ml methylene chloride (BDH, HPLC Grade), aliquots of 350 $\mu$l were dispensed into small screw-cap vials with Teflon-coated septa. The vials were wrapped with Parafilm and stored at 4° C.

Chloroform (Associated Chemical Enterprises, Chemically Pure Grade)

Methylene chloride (BDH, HPLC-Grade)

Reagents A,B,C and E were prepared fresh prior to experiments, taking all the necessary safety precautions.

Countercurrent Distribution Apparatus

Figure 4:
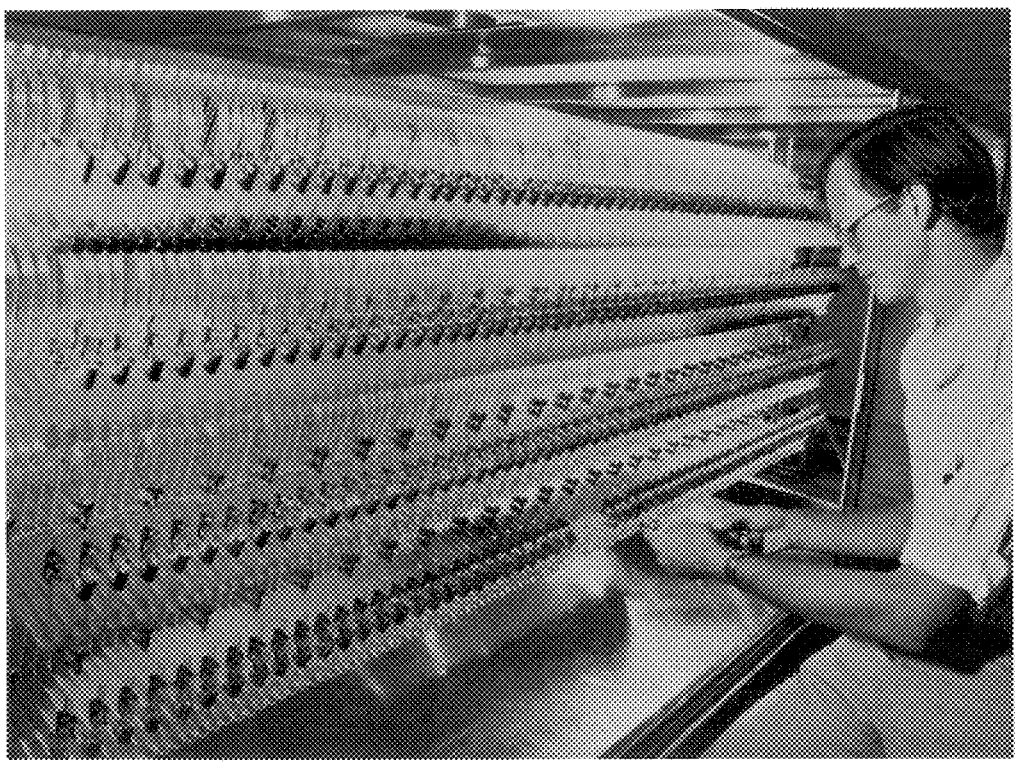
FIG. 4 is a photograph of a countercurrent distribution apparatus for use in the purification of mycolic acids.

A countercurrent apparatus produced by H O POST, Instrument Company Inc., Middle Village, N.Y. was used during the investigations. A photograph of the apparatus available at the Department of Biochemistry at the University of Pretoria, is presented in FIG. 4. The "trains" in this model consisted of 2×250 inter-connected tubes.

Any other chemically-engineered system of countercurrent distribution may, of course, be used.

Infra-Red Spectrometer

Infra-red spectrum analyses of countercurrent-purified mycolic acids were carried out using a BOMEM Michelson 100 FTIR apparatus and a Hewlett Packard plotter.

METHODS

The following methods were used in the experimental work:

Cultivation of the Bacterial Strain

The bacteria were cultivated at 37° C. using:
Dubos broth
Löwenstein-Jensen medium (slants), and
Middlebrook 7H-10 agar medium (slants).

The inoculation of the media and the handling of the Mycobacterium cultures, were carried out according to the procedures recommended by Kent and Kubica (1985) in a Guide for the Level III Laboratory, Public Health U.S. Department of Health and Human Services, Atlanta.

Preparation of Lipid Cell-Wall Components from Bacterial Samples

The preparation of bacterial samples comprised three steps:
harvesting of the Mycobacteria cells;
saponification and
extraction of fatty acids.

Harvesting was done by scraping the bacterial growth from the surface of media slants. The growth can also be collected from liquid cultures by centrifugation. Homogenous bacterial suspensions were prepared in Reagent A, by shaking or vortexing the harvested cells with sterile glass beads, to a final concentration of approximately $1 \times 10^7$ cfu*/ml.

*cfu=colony forming units

Saponification of the Mycobacteria in Reagent A was carried out in an autoclave at 121° C., for one hour.

The saponification, extraction and derivatization of fatty acids were carried out as described by Butler, Jost and Kilburn (1991).

Extraction of Lipid Cell-Wall Compounds

The samples were allowed to cool and 1,5 ml Reagent B was introduced to each sample. After vortexing, the pH of each sample was checked and if necessary, adjusted to pH 1 with reagent B.

Subsequently, 2,0 ml chloroform was added to each sample and vortexed for 30 seconds. The layers were allowed to separate. The bottom layers were removed with Pasteur pipettes, transferred to WISP vials and evaporated to dryness at 85° C. in a heat block-evaporator under a stream of nitrogen. To neutralize traces of acid carried over, 100 µl of reagent C was added to each sample and the fluid evaporated to dryness at 85° C. on a heat block-evaporated under a stream of nitrogen. The samples were stored in the dark, under acetone at 4° C. until used or analyzed by HPLC.

Derivatization of Fatty Acids for HPLC Analysis

Extracted and purified fatty acids (mycolic acids) were derivatized as follows:

Acetone was removed form the samples by evaporation on a heat block-evaporator at 85° C., under a stream of nitrogen. To each cooled sample 2,0 ml Reagent A was added. The samples were vortexed for 30 seconds, Reagent B (1,5 ml) was introduced, the samples were mixed again and the pH adjusted to pH 1,0, if required. Subsequently, chloroform (2,0 ml) was introduced, followed by the addition of 100 µl of Reagent C. The capped samples were vortexed for 30 seconds, heated for 5 minutes at 85° C. on a heat block-evaporated and dried by introducing a stream of nitrogen.

Derivatization was carried out by introducing 1,0 ml chloroform and 100–150 µl of Reagent D, vortexing the samples for 30 seconds, sealing the vials containing the samples and placing them on a heat block-evaporator at 85° C. for 20 minutes. Reagent E (1,0 ml) was added after the samples were cooled. The samples were vortexed again for 30 seconds and the layers allowed to separate. The bottom layers were removed with Pasteur pipettes and transferred to WISP-vials. The vials were placed on a heat block-evaporator and their contents evaporated to dryness at 85° C. using a stream of nitrogen.

The residues were resuspended in 0,212 g (which corresponds to 160 µl) methylene chloride, capped and vortexed. Each reconstituted sample, into which 5 µl HPLC internal standard was introduced, was filtered through a 0,45 µm membrane filter into an amber-coloured WISP-vial. The recapped vials were stored at 4° C. until ready for HPLC analysis.

HPLC Analysis and Quantification of Mycolic Acids

For the HPLC analysis 25 µl from each sample (maintained on ice during handling), was analyzed. Control samples, i.e. 25 µl of filtered methylene chloride, were run prior to each set of samples analyzed. If a large number of samples was analyzed, in order to validate the reliability of the HPLC apparatus, control samples were run after every three or four test samples.

The reverse-phase HPLC analyses were carried out using a Waters System High Performance Liquid Chromatography apparatus (Milford, Mass.) consisting of:
System Controller (Waters 600 E);
Detector (Waters 486 Tunalde);
Autosampler (Waters 712 WISP);
Data module (Microsep M 741);
Column Waters (Nova-Pak C18 60 A, 4 µm, 3,9×150 mm) and an end connector set for steel cartridge columns;
Guard column (Guard-Pak/Nova-Pak C18).
Running conditions were:
Mobile phase:
Solvent A: HPLC Grade Methanol
Solvent B: HPLC Grade Methylene chloride
Flow Rate: 2,5 ml/min
Column temperature: 30° C.

The detector was set at 260 nm.

The HPLC gradient initially comprised 98% (v/v) methanol (Solvent A) and 2% (v/v) methylene chloride (Solvent B). The gradient was increased linearly to 80% A and 20% B at one minute; 35% A and 65% B at ten minutes, held for 5 seconds and then decreased over 10 sec back to 98% A and 2% B. This ratio was maintained for 6 minutes to allow for stabilization of the system prior to injection of the next sample.

Mathematical quantification of mycolic acids was carried out by comparing the combined peak areas of the tested samples to the peak area of the introduced quantity of the High Molecular Weight Internal HPLC Standard.

Purification of Mycolic Acids and Group Separation of Other Fatty Acids

A countercurrent distribution train comprising 25 tubes, numbered 0–24, was used in the experiment. Into a buffer reservoir approximately 900 ml of the upper phase was introduced.

Into tube number 0, a sample of the crude cellular extract of M. tuberculosis obtained from a large-scale extraction experiment (30–150 mg), dissolved in 10 ml of the lower phase and 10 ml of the upper phase was introduced. Into the remaining 24 tubes aliquots of 10 ml of the lower phase were introduced. Upper phase, in volumes of 10 ml per cycle, was automatically dispensed into tube number 0, repeatedly over 25 cycles resulting in approximately 16 hour operation. Thus, twenty five countercurrent cycles were performed, with each cycle consisting of 20 mixing pendula and 40 minutes phase separation time.

Figure 5:
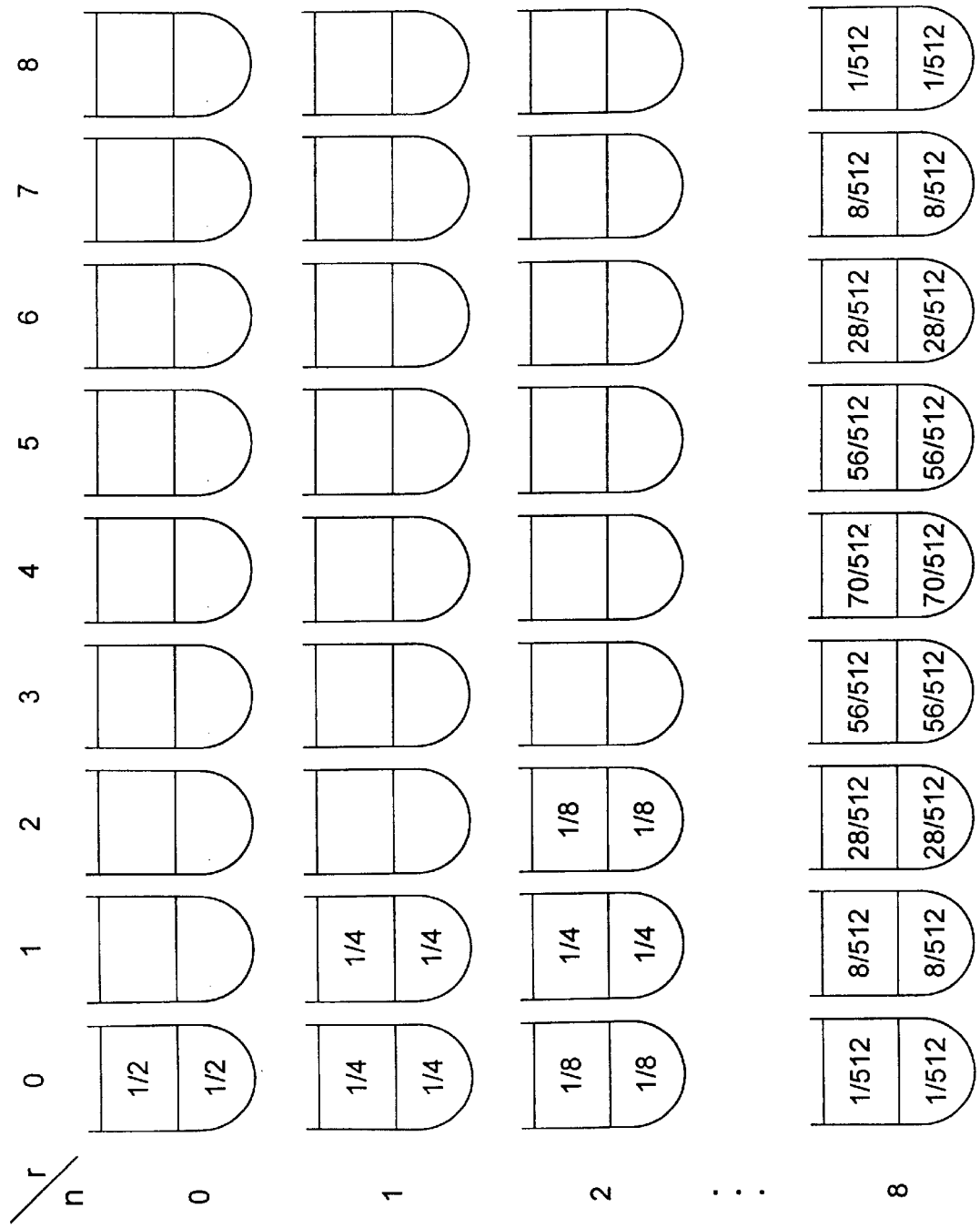
FIG. 5 is a schematic representation of a countercurrent distribution system with nine test tubes.

The process is graphically illustrated in FIG. 5.

With each transfer, any solute originating from the sample and present in the upper phase is carried into the succeeding tube. After the completion of twenty five transfers, the separated solute fractions should be distributed along the train of 25 tubes.

To establish the distribution of fatty acids among the twenty five tubes, the emulsification patterns in upper and lower phases were observed within the tube train and fractions were determined accordingly.

The countercurrent-separated material was then withdrawn from the tubes using a 50 ml glass syringe, with a Teflon tubing attached. The material was pooled into seven fractions, dried individually under vacuum in a Buchi evaporator at 70° C., the dried material redissolved in either chloroform, methanol or water (in approximately 5 ml), transferred into amber WISP-vials and stored at 4° C. until required.

Acetone Extraction

In order to remove any residual impurities still present in the countercurrent-purified material, an additional extraction with acetone was carried out as follows:

to a sample of the purified mycolic acids (approximately 5,0 mg) placed in a WISP vial, an aliquot of acetone (3,0 ml) was introduced and the sample was mixed by vortexing. After sedimentation, the acetone was removed by aspiration and the process repeated two times. The finally purified and extracted sample was stored under acetone.

Yield of the Mycolic Acids Purified by Countercurrent Separation

In order to calculate the approximate yield of purification/separation, the weighed amount of the mycolic acids present in the samples obtained after the countercurrent separation/purification was compared to the amount of these compounds present in the crude cellular extract introduced into the countercurrent apparatus, calculated from the relative peak areas of the mycolic acids peak cluster and that from the peak area of the standard in the HPLC chromatogram of the crude cellular extract.

Alternatively, the peak area from the mycolic acids peak cluster of the HPLC chromatogram of the purified mycolic acids was compared to that obtained for the crude extract to estimate the yield and purity of the product.

Infra-Red Spectrum Analysis of the Purified Mycolic Acids

Infra-red spectrum analysis was carried out using a countercurrent-purified sample (1 mg) extracted from M. tuberculosis. Mycolic acids were dissolved in 1 ml HPLC grade chloroform and injected into the liquid vial. As a reference HPLC grade chloroform was used. The absorption of the reference was subsequently subtracted from the sample profile.

RESULTS

Purification of Mycolic Acids from M. Tuberculosis

Figure 6:
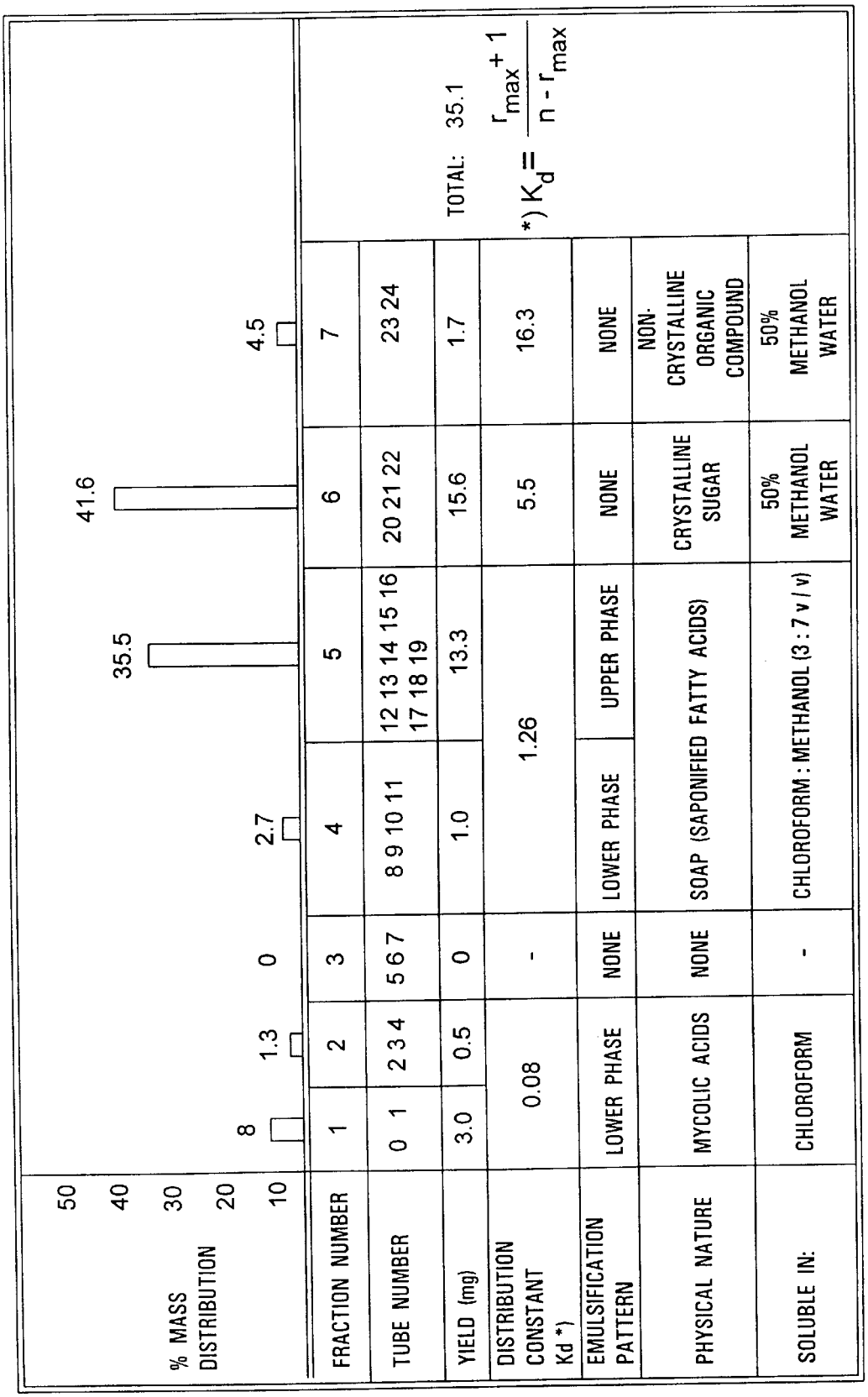
FIG. 6 is a chart showing the distribution of components separated from a crude mycolic extract of *M. tuberculosis* by countercurrent distribution in accordance with the invention.

The material (37,5 mg) extracted from M. tuberculosis H37Rv (ATCC 27294), according to the method proposed by Butler, Jost and Kilburn (1991) for the isolation of mycolic acids, was found to contain less than 10% mycolic acids after countercurrent extraction of 25 cycles (FIG. 6). Mycolic acids were identified by HPLC in fraction 1 and 2 only, which together comprised 9,3% of the dry mass of the crude extract that was loaded on the countercurrent apparatus. Mycolic acids exhibited a distribution coefficient of only 0,08, which allowed complete separation from the shorter saponified fatty acids at a distribution coefficient of around 1,26 (FIG. 6). The mycolic acid fraction was easily recognised by its emulsification pattern in the countercurrent tube train in the first few tubes, followed by 3 tubes which did not contain any significant amount of material. The saponified short chain fatty acids could be identified in 4 tubes containing emulsion in the lower phase, immediately followed by 8 tubes with emulsion in the upper phase, indicative of the equilibrium between dissociated (upper phase emulsion) and protonated (lower phase emulsion) fatty acids during the separation. The remaining fractions 6 and 7 could not be analyzed by HPLC due to the fact that they were not soluble in chloroform, a property which also excludes the possibility of their containing any mycolic acids.

Figure 8A:
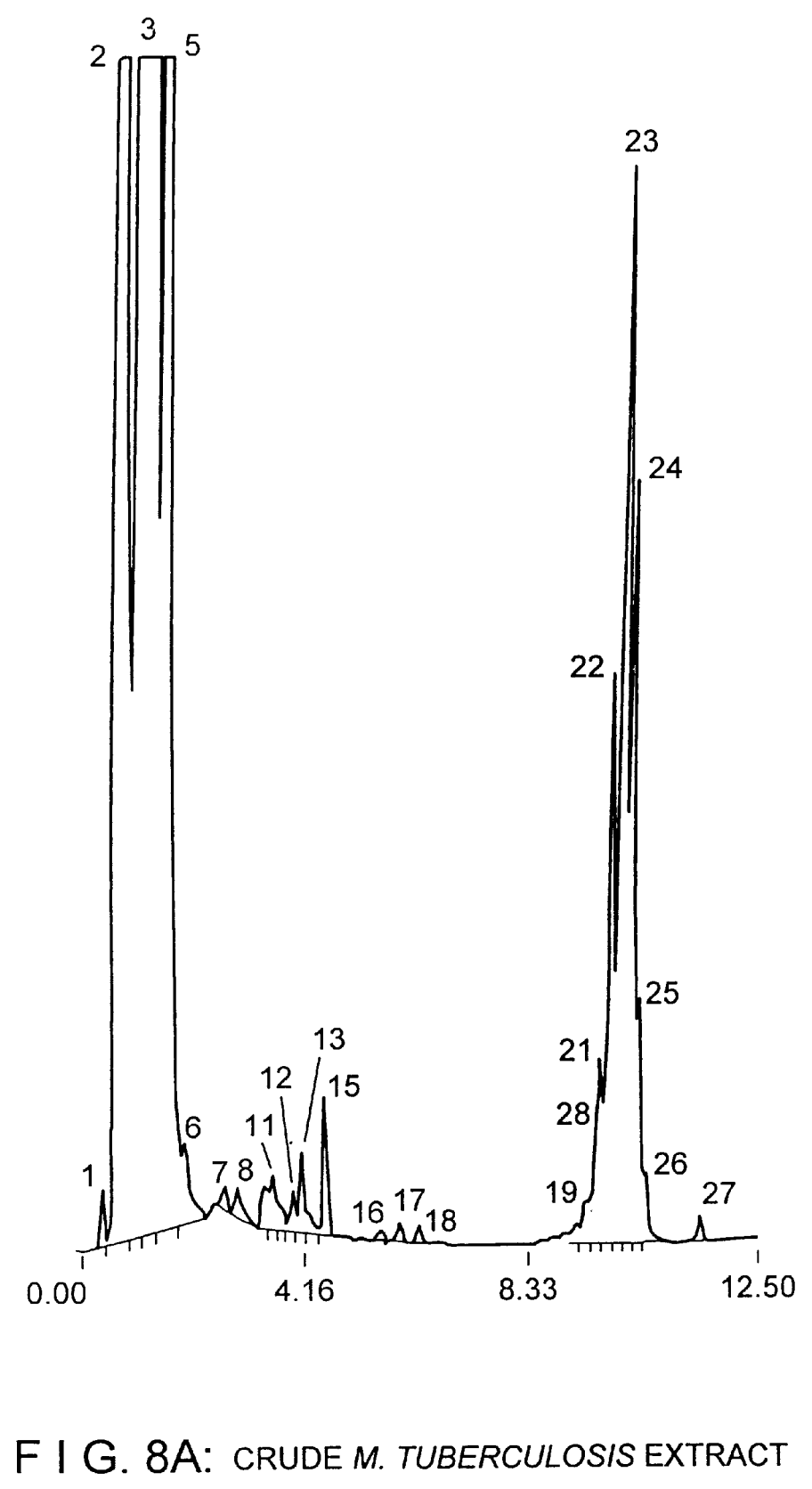

The HPLC profiles/chromatograms of the crude extracts originating from M. tuberculosis, the reagents used and the bacterial medium are presented in FIGS. 8A, 8B and 8C, respectively.

Mycolic acids, purified by countercurrent distribution, still contained some contaminating material which could be detected on HPLC at a retention time spanning from 4–6 minutes (FIG. 12A). A diagram showing how acetone was employed to extract these impurities from the samples, is given in FIG. 3. The diagram represents a systematic investigation on a single large batch of crude extract originating from M. tuberculosis to allow direct comparison of HPLC profiles and calculate relative yields.

The contaminating peaks did not arise from the reagents used in the extraction and purification procedures (FIG. 12B), but could stem from the ingredients of the bacterial culture medium (FIG. 12C). When extraction with acetone was carried out on the crude extracts prior to countercurrent purification, some degree of extraction of impurities from bacterial (FIG. 9A) and growth medium (FIG. 9C) samples was observed, but it did not suffice to remove all impurities from the final countercurrent-purified product (FIG. 11A). When the dried, countercurrent-purified mycolic acids were extracted with acetone, it appeared that the impurities were soluble in the acetone (FIGS. 13A and 13C). The HPLC analysis of the acetone-rinsed mycolic acids fraction indicated that this fraction was free from any impurities (FIG. 14A), other than those which were due to the derivatization reagents and which could be observed in control extracts from purification reagents (FIG. 14B) and growth media (FIG. 14C).

On the basis of these results it is claimed that a crude extract of Mycobacteria, obtained according to the method of Butler, Jost and Kilburn (1991) and purified by countercurrent separation as described above followed by acetone extraction, yields mycolic acids free from any impurities detectable by HPLC (FIG. 14A).

The purity of mycolic acids was also assessed by comparing the mass of the countercurrent-purified material with the calculated yield of mycolic acids based on the surface of the absorbance peaks on the HPLC chromatogram. Countercurrent-purified mycolic acids before acetone rinsing (FIG. 12A; 0,3 mg) were analyzed by HPLC after derivatization as described above. When the surface of the absorption peak of the internal standard (representing 5,01 $\mu$g) was compared to that of the mycolic acids, a yield of 0,27 mg of mycolic acids was calculated, representing 90% of the weighed material. Taking into consideration that some material is lost by transfer of phases between vials during the derivatization and extraction process, and that some contamination is removed by acetone extraction, the purity of the mycolic acids fraction represented by the HPLC profile in FIG. 14A may be regarded as approaching 100%.

Figure 7:
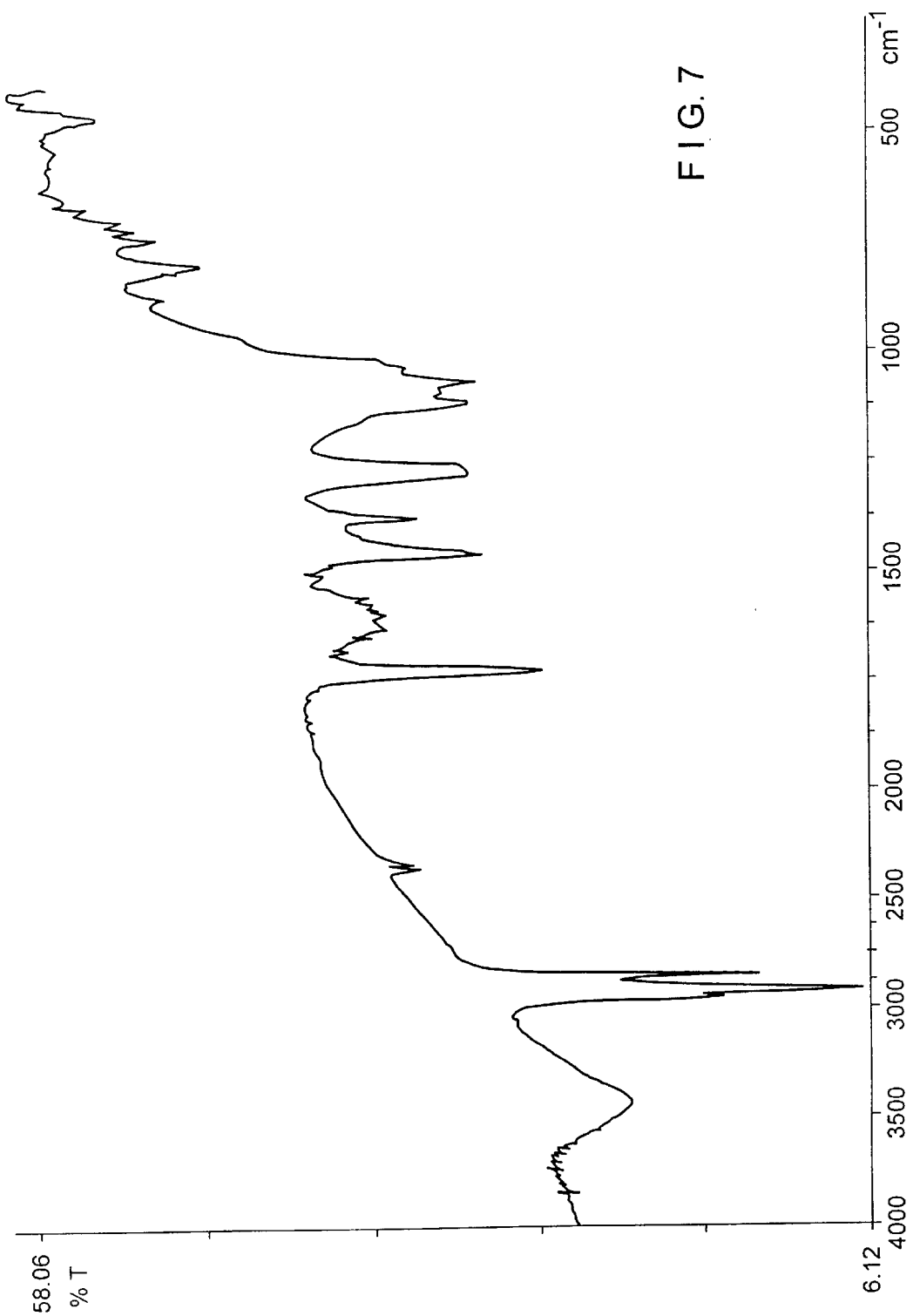
FIG. 7 is an infra-red spectrum of mycolic acids, originating from *M. tuberculosis,* that have been purified in accordance with the invention.

Countercurrent purification yielded mycolic acids as methyl ester derivatives. This is evident from the infrared spectrum of the countercurrent purified mycolic acids before acetone extraction (FIG. 7) and by HPLC analysis when resaponification in Reagent A after purification is omitted (results not included). The addition of Reagent A restores the free acid and is required to effect derivatization with para-bromophenacylbromide.

Purification of Mycolic Acids from M. Vaccae

The growth of M. vaccae was extracted and purified in the same way as that of M. tuberculosis. HPLC analysis of the crude extract (FIG. 15B) showed three peak clusters with retention times greater than 5 minutes and a broad reagents/short chain fatty acids peak cluster at a retention time shorter than 2 minutes. After countercurrent purification and rinsing with acetone, two clusters of peaks remained at retention times greater than 5 minutes on the HPLC column (FIG. 15B). In addition, the reagents/short chain fatty acids peak cluster was considerably narrower, leaving no traces of detectable impurities. On a mass basis, the mycolic acids were purified to approximately 5% yield, whereas 4,3% yield was calculated by comparing the areas of the mycolic acids peak clusters of the HPLC chromatograms of the crude and purified mycolic acids extracts.

Similar results were obtained with countercurrent purified mycolic acids extracted from M.avium (ATCC 25291).

Besides somewhat lower yields, these results are similar to those found for the purification of mycolic acids from M. tuberculosis, thus demonstrating the wider application of the countercurrent purification method of mycolic acids among species of Mycobacteria.

REFERENCES

Antonucci, G., H., Girardi, M. C., Raviglione and G. Ippolito. 1995. Risk factors for tuberculosis in HIV-infected persons: a prospective cohort study. *JAMA, The Journal of the American Medical Association*, 274, 143–148.

Arya, S. C. 1993. Serologic diagnosis of tuberculosis through assays of lipoarabinomannan antigen or antibody or lysozyme level. *J. Clin. Microbiol.*, 31, 2836–2837.

Ballew, K. A. and D. M., Becker. 1995. Tuberculosis screening in adults who have received bacille Calmette-Guerin vaccine. *Southern Med. J.*, 88, 1025–1030.

Bahr, G. M., J. L. Stanford, T. D. Chugh et al., 1990a. An investigation of patients with pulmonary tuberculosis in Kuwait in preparation for studies of immunotherapy with *Mycobacterium vaccae. Tubercle*, 71, 77–86.

Bahr, G. M., M. A. Shaaban, M. Gabriel et al., 1990b. Improved immunotherapy for pulmonary tuberculosis with *Mycobacterium vaccae. Tubercle*, 71, 259–266.

Beckman, E. M., S. A. Porcelli, C. T. Morita et al., 1994. Recognition of a lipid antigen by CD1-restricted $\alpha\beta^+$ T cells. *Nature*, 372, 691–694.

Beckman, E. M., S. A. Porcelli, C. T. Morita, S. Furlong and M. B. Brenner. 1995. DC1 molecules: a third pathway of antigen presentation. In: *Proceedings of the IX-th International Congress of Immunology, San Francisco*, July 23–29, 4190.

Berger, F. M., Bona, C., Lechevalier, M. P., 1995. Immunological adjuvant and process for preparing the same. U.S. Pat. No. 4,877,612.

Besra, G. S., D. E. Minnikin, M. J. Simpson, M. S. Baird, P. R. Wheeler and C. Ratledge. 1993. The synthesis of methyl 4-(2-octadecylcyclopropen-1-yl)butanoate: a possible inhibitor in mycolic acid biosynthesis. *Chemistry and Physics of Lipids*, 66, 35–40.

Beyers, A. D., P. R. Donald, P. D. van Helden et al., 1996. Tuberculosis research—the way forward. *SAMJ, South African Medical Journal*, 86, 30–33.

Bloomfield, G. 1995. Diagnosis of tuberculosis. In: *Tuberculosis: Trends and Opportunities*, PJB Publications Ltd, Chpt. 4, pp 59–84.

Blumberg, L., B. Miller and H. J. Koornhof. 1994. Multiple drug resistant Mycobacterium tuberculosis. Book of Abstracts: *Tuberculosis—Towards* 2000. A scientific conference and workshops on the short-term future of tuberculosis in the developing world, with particular emphasis on Africa. Pretoria, South Africa, March 13–17, 1994.

Brennan, P. J. 1984. Antigenic peptidoglycolipids, phospholipids and glycolipids. In: *The Mycobacteria—A sourcebook*, chpt 18, pp 467–489. Publ. Marcel Dekker, Inc., New York and Basel.

Brennan, P. J. and H. Nikaido, 1995. The envelope of Mycobacteria. *Annu. Rev. Biochem.* 64, 29–63.

Butler, W. R., K. C. Jost and J. O. Kilburn. 1991. Identification of Mycobacteria by High-Performance Liquid Chromatography. *J. Clin. Microbiol*, 29, (11), 2468–2472.

Cantwell, M. C. and N. J. Binkin. 1994. Tuberculosis and HIV in sub-Saharan Africa: Can a good tuberculosis control program make a difference? Book of Abstracts: *Tuberculosis—Towards* 2000. A scientific conference and workshops on the short-term future of tuberculosis in the developing world, with particular emphasis on Africa. Pretoria, South Africa, March 13–17, 1994.

Chaparas, S. D. 1984. Immunologically based diagnostic tests with tuberculin and other mycobacterial antigens. In: *The Mycobacteria—A sourcebook*, chpt 9, pp 195–220. Publ. Marcel Dekker, Inc., New York and Basel.

Colditz, G. A., T. F. Brewer, C. S. Berkey et al., 1994. Efficacy of BCG vaccine in the prevention of tuberculosis: meta analysis of the published literature. *JAMA, The Journal of the American Medical Association*, 271, 698–702.

Cole, S. 1995. The Challenge of Tuberculosis: Statements on Global Control and Prevention. Basic science. (Lancet Conference). *The Lancet*, 346, 816–817.

Collins, F. M. 1994. The immune response to mycobacterial infection—development of new vaccines. *Veterinary Microbiology*, 40, 95–110.

Daniel, T. M. 1984. Soluble mycobacterial antigens. In: *The Mycobacteria— A sourcebook*, chpt 17, pp 417–465. Publ. Marcel Dekker, Inc., New York and Basel.

Darbyshire, J. H. 1995. Tuberculosis: old reasons for a new increase? *Br. Med. J.,* 310, 954–955.

Davies, G. R., D. Wilkinson and M. Colvin. 1996. HIV and tuberculosis. *SAMJ, South African Medical Journal,* 86, 91.

De Cock, K. M. 1994. Impact of Interaction with HIV. In: *Tuberculosis Back to the Future,* London School of Hygiene & Tropical Medicine, Third Annual Public Health Forum; Editors: J. D. H. Porter and K. P. J. McAdam. Publ. John Wiley & Sons, Chichester, New York, Brisbane, Toronto, Singapore, Chpt 2, pp 35–52.

De Cock, K. M., B. Soro, I. M. Coulibaly and S. B. Lucas. 1992. Tuberculosis and HIV infection in sub-Saharan Africa. *JAMA, The Journal of the American Medical Association,* 268, 1581–1587.

Deshpande, R. H., M. B. Khan, D. A. Bhat and R. G. Navalkar. 1994. Purification and partial characterisation of a novel 66-kDA seroreactive protein of *Mycobacterium tuberculosis* $H_{37}Rv$. *J. Med. Microbiol.,* 41, 173–178.

Dolin, P. J,, M. C. Raviglione and A. Kochi. 1994. Global tuberculosis incidence and mortality during 1990–2000. *Bulletin of the World Health Organisation,* 72 (2), 213–230.

Etemadi, A., R. Farid and J. L. Stanford. 1992. Immunotherapy for drug resistant tuberculosis. *The Lancet,* 340, 1360–1361.

Fauci, A. S. 1995. New science aimed at an ancient killer. *JAMA, The Journal of the American Medical Association,* 274, 786.

Fine, P. E. M. 1994. Immunities in and to tuberculosis: implications for pathogenesis and vaccination. In: *Tuberculosis Back to the Future,* London School of Hygiene & Tropical Medicine, Third Annual Public Health Forum; Editors: J. D. H. Porter and K. P. J. McAdam. Publ. John Wiley & Sons, Chichester, New York, Brisbane, Toronto, Singapore, Chpt 1, pp 13–33.

Godfrey-Faussett, P. 1994. Of molecules and men: the detection of tuberculosis, past, present and future. In: *Tuberculosis Back to the Future,* London School of Hygiene & Tropical Medicine, Third Annual Public Health Forum; Editors: J. D. H. Porter and K. P. J. McAdam. Publ. John Wiley & Sons, Chichester, New York, Brisbane, Toronto, Singapore, Chpt 4, pp 79–96.

Goren, M. B. 1972. Mycobacterial Lipids: Selected Topics. *Bacteriological Reviews,* 36, 33–64.

Grange, J. M. 1988. Chapter 2: The genus Mycobacterium. In: *Mycobacteria and Human Disease.* Edward Arnold (Publishers) Ltd, London, UK; Victoria, Australia; Baltimore, Md., USA, pp 8–17.

Grosset, J. 1995. The Challenge of Tuberculosis: Statements on Global Control and Prevention. Treatment in developed countries. (Lancet Conference). *The Lancet,* 346, 810–812.

Henderson C. W. 1995. WHO Reports 1,000 New TB Cases Every Hour. *AIDS Weekly,* May 15, 1995.

Hershfield, E. S. 1995. The Challenge of Tuberculosis: Statements on Global Control and Prevention. Prevention in the developed countries. (Lancet Conference). *The Lancet,* 346, 813–814.

Holler, A. 1995. ID Vaccine and Pasteur Merieux—Connaught Complete Licensing and Collaboration Agreement on Tuberculosis Vaccine. *Business Wire,* Oct. 2, 1995, Vancouver, Canada.

Huebner, R. E. and K. G. Castro. 1995. The changing face of tuberculosis. *Annu. Rev. Med.* 46, 47–55.

Hunter, S. W., H. Gaylord and P. J. Brennan. 1986. Structure and antigenicity of the phosphorylated lipopolysaccharide antigens from the leprosy and tubercule bacilli. *J. Biol. Chem.* 261, 12345–12351.

Kent, P. T. and G. P. Kubica. 1985. Public Health Mycobacteriology—a Guide for the Level III Laboratory, Public Health U.S. Department of Health and Human Services, Public Health Service, Centers for Disease Control, Laboratory Program Office, Atlanta, Ga.

Law, M. R., J. K. Morris, N. Bhatii, R. Halliday and J. Moore-Gillon. 1995. Reasons for increased incidence of tuberculosis. *British Med. J.* 311, 688.

Mangtani, P., D. J. Jolley, J. M. Watson and L. C. Rodrigues. 1995. Socioeconomic deprivation and notification rates for tuberculosis in London during 1982–1991. *Br. Med. J.* 310, 963–966.

Mc Neil, M., D. Chatterjee, S. Wu Hunter and P. J. Brennan. 1989. Mycobacterial glycolipids: isolation, structure, antigenicity, and synthesis of neoantigens. In: *Methods in Enzymology,* 179, pp 215–242.

Misaki, A., I. Azuma and Y. Yamamura. 1987. Structural and immunochemical studies on D-arabino-D-mannans and D-mannans of *Mycobacterium tuberculosis* and other Mycobacterium species. *J. Biochem.* 82, 1759–1770.

Mofenson, L. M., E. M. Rodriguez, R. Hershow et al., 1995. *Mycobacterium tuberculosis* infection in pregnant and nonpregnant women infected with HIV in the Women and Infant Transmission study. *Arch. Intern. Med.,* 155, 1066–1072.

Morita, C. T., E. Beckman, J. F. Bukowski et al., 1995. Direct presentation of nonpeptide prenyl pyrophosphate antigens to human τδ T cells. In: *Proceedings of the IX-th International Congress of Immunology, San Francisco,* July 23–29, 1495.

Morse, D. L. 1994. Multidrug resistance; The New York experience. In: *Tuberculosis Back to the Future,* London School of Hygiene & Tropical Medicine, Third Annual Public Health Forum; Editors: J. D. H. Porter and K. P. J. McAdam. Publ. John Wiley & Sons, Chichester, New York, Brisbane, Toronto, Singapore, Chpt 11, pp 225–237.

Murray, C. J. L. 1994. Resource allocation priorities: value for money in tuberculosis. In: *Tuberculosis Back to the Future,* London School of Hygiene & Tropical Medicine, Third Annual Public Health Forum; Editors: J. D. H. Porter and K. P. J. McAdam. Publ. John Wiley & Sons, Chichester, New York, Brisbane, Toronto, Singapore, Chpt 9, pp 193–211.

Mwinga, A. 1995. The Challenge of Tuberculosis: Statements on Global Control and Prevention. Treatment in developing countries. (Lancet Conference). *The Lancet,* 346, 812–813.

O'Brien, R. 1995. The Challenge of Tuberculosis: Statements on Global Control and Prevention. Prevention in developing countries. (Lancet Conference). *The Lancet,* 346, 814–816.

Onybebujoh, P. V. C., T. Abdulmumini, S. Robinson, G. A. W. Rook and J. L. Stanford. 1995. Immunotherapy with *Mycobacterium vaccae* as an addition to chemotherapy for the treatment of pulmonary tuberculosis under difficult conditions in Africa. *Respir. Med.,* 89, 199–207.

Petit, J-F and E. Lederer. 1984. The structure of the mycobacterial cell wall. In: *The Mycobacteria,* A Sourcebook. Editors: G. P. Kubica and L. G. Wayne, Marcel Dekker, Inc, New York and Basel, Part A, Chpt. 12, 301–339.

Pretorius, G. S., F. A. Sirgel, H. S. Schaaf, P. D. van Helden and T. C. Victor. 1996. Rifampicin resistance in Mycobacterium tuberculosis—rapid detection and implications in chemotherapy. *SAMJ, South African Medical Journal,* 86, 50–55.

Prior, J. G., A. A. Khan, K. A. V. Cartwright, P. A. Jankins and J. L. Stanford. 1995. Immunotherapy with *Mycobacterium vaccae* combined with second line chemotherapy in drug-resistant abdominal tuberculosis. K. Infect. 31, 59–61.

Public Health Reports, 1995. 110, 108–109.

Raviglione, M. C., D. E Snider and A. Kochi. 1995 Global epidemiology of tuberculosis—morbidity and mortality of a worldwide epidemic. *JAMA, The Journal of the American Medical Association,* 273, 220–226.

Richeldi, L., S. Barnini and C. Saltini. 1995. Molecular diagnosis of tuberculosis. *Eur. Respir. J. Supplement* 8/20, 689–700.

Rosat, J. P., E. M. Beckman, S. Porcelli and M. B. Brenner. 1995. CD-1 restricted τδ T cell response to mycobacterial antigens. In: *Proceedings of the IX-th International Congress of Immunology, San Francisco,* July 23–29, 1488.

Schaberg, T., B. Reichert, T. Schulin, H. Lode, and H. Mauch. 1995. Rapid drug susceptibility testing of *Mycobacterium tuberculosis* using conventional solid media. *Eur. Respir. J.,* 8, 1688–1693.

Sieling, P., D. Chatterjee, T. Pirgozy et al., 1995. CD1 presentation of non-peptide ligands from microbial pathogens to αβ TCR T-cells. In: *Proceedings of the IX-th International Congress of Immunology, San Francisco,* July 23–29, 2726.

Snider, D. E. 1994. Tuberculosis: the world situation. History of the disease and efforts to combat it. In: *Tuberculosis, Back to the Future.* London School of Hygiene & Tropical Medicine, Third Annual Public Health Forum. Editors: J. D. H. Porter and K. P. J. McAdam. John Wiley & Sons (Publishers), Chichester, UK, Chpt. 1, pp 13–33.

South African Provisional Patent Application Ser. No. 94/25/75: "A method for detecting the presence of a Mycobacterium species and a kit and antibodies for used therein".

South African Patent Application Ser. No. 95/30/77: "A method for detecting the presence of a Mycobacterium species and a kit and antibodies for used therein".

Stanford, J. L., G. A. W. Rook, G. M. Bahr et al., 1990a. *Mycobacterium vaccae* in immunoprophylaxis and immunotherapy of leprosy and tuberculosis. (Review). *Vaccine,* 8, 525–530.

Stanford, J. L., G. M. Bahr, G. A. W. Rook et al., 1990b. Immunotherapy with *Mycobacterium vaccae* as an adjunct to chemotherapy in the treatment of pulmonary tuberculosis. *Tubercle,* 71, 87–93.

Stanford, J. L. and J. M. Grange. 1993. New concepts for the control of tuberculosis in the twenty first century. *J. R. Coll. Physicians Lond.,* 27, 218–223.

Stanford, J. L. and J. M. Grange. 1994. The promise of immunotherapy for tuberculosis. *Respir. Med.* 88, 3–7.

The Merck Index, 1989. Editors: S. Budavari, M. J. O'Neil, A. Smith and P. E. Heckelman, Eleventh Edition, p 6236.

Torres, R. A., S. Mani, J. Altholz and P. W. Brickner. 1990. Human Immunodeficiency Virus Infection Among Homeless Men in a New York City Shelter. *Arch. Intern. Med.,* 150, 2030–2036.

Torres, M., P. Mendez-Sampeiro, L. Jimenez-Zamudio et al., 1994. Comparison of the immune response against *Mycobacterium tuberculosis* antigens between a group of patients with active pulmonary tuberculosis and healthy household contacts. *Clin. Exp. Immunol.,* 96, 75–78.

Vlaspolder, F., P. Singer and C. Roggeveen. 1995. Diagnostic value of an amplification method (Gen-Probe) compared with that of culture for diagnosis of tuberculosis. *J. Clin. Microbiol.,* 33, 2699–2703.

Voelker, R. 1995. New initiative for global TB control. *JAMA, The Journal of the American Medical Association,* 274, 1255–1257.

Walter, H. and G. Johansson. 1986. Partitioning in Aqueous Two-Phase Systems: An Overview. *Analytical Biochemistry,* 155, 215–242.

Weil, D. E. C. 1994. Drug supply: meeting a global need. In: *Tuberculosis, Back to the Future.* London School of Hygiene & Tropical Medicine, Third Annual Public Health Forum. Editors: J. D. H. Porter and K. P. J. McAdam. John Wiley & Sons (Publishers), Chichester, UK, Chpt 6, pp 123–143.

Wheeler, P. R., G. S. Besra, P. J. Brennan and D. E. Minnikin. 1994. Mycolic acids biosynthesis—the early stages. Book of Abstracts: *Tuberculosis—Towards 2000.* A scientific conference and workshops on the short-term future of tuberculosis in the developing world, with particular emphasis on Africa. Pretoria, South Africa. Mar. 13–17, 1994.

WHO Report on the Tuberculosis Epidemic, World Health Organisation, WHO/TB/1995/183.

Wilkinson, D. and K. M. de Cock. 1996. Tuberculosis control in South Africa—time for a new paradigm? *SAMJ. South African Medical Journal,* 86, 33–35.

Wilkinson, D. and A. J. Moore. 1996. HIV-related tuberculosis in South Africa—clinical features and outcome. *SAMJ, South African Medical Journal,* 86, 64–67.

Yanez, M. A., M. P. Coppola, D. A. Russo et al., 1986. Determination of mycobacterial antigens in sputum by enzyme immunoassay. *J. Clin. Microbiol,* 23, 822–825.

Yew, W. W. and C. H. Chau. 1995. Drug-resistant tuberculosis in the 1990s. (Review). *Eur. Respir. J.,* 8, 1184–1192.

What is claimed is:

1. A method of purifying mycolic acids, salts thereof or derivatives thereof, said method consisting essentially of:
   a) providing a mixture comprising the mycolic acids, salts thereof or derivatives thereof and contaminants;
   b) dissolving the mixture in bi-phasic solvent to form a dissolved mixture comprising the mycolic acids, salts thereof or derivatives thereof and contaminants;
   c) purifying the mycolic acids, salts thereof or derivatives thereof by subjecting the dissolved mixture to counter-current distribution separation comprising a sufficient number of cycles to separate the mycolic acids, salts thereof or derivatives thereof from the contaminants; and
   d) removing the separated, purified mycolic acids, salts thereof or derviatives thereof from the bi-phasic solvent.

2. The method according to claim 1, wherein the mixture provided in step (a) is an extracted mixture or synthetic mixture.

3. The method according to claim 1, wherein the mycolic acids are derived from a bacterium selected from the group consisting of the genera Mycobacterium, Corynebacterium, Nocardia and Rhodococcus.

4. The method according to claim 3, wherein the bacterium is selected from the species *M. tuberculosis, M. avium* and *M. vaccae.*

5. The method according to claim 1, wherein the mixture provided in (a) is a saponified mixture comprising mycolic acids or salts thereof and contaminants.

6. The method according to claim 1, wherein the mycolic acids derivative is a mycolic acids ester.

7. The method according to claim 6, wherein the mycolic acids derivative is a methyl ester derivative.

8. The method according to claim 1, wherein the contaminants are selected from the group consisting of bacterial cellular extract and bacterial culture medium.

9. The method according to claim 8, wherein the bacterial cellular extract is from a bacterium selected from the group consisting of the genera Mycobacterium, Corynebacterium, Nocardiaand Rhodococcus.

10. The method according to claim 1, wherein the bi-phasic solvent comprises chloroform, methanol and water.

11. The method according to claim 10, wherein the bi-phasic solvent comprises an upper liquid phase and a lower liquid phase.

12. The method according to claim 11, wherein each cycle comprises the step of mixing and equilibrating the upper and lower phases of the bi-phasic solvent.

13. The method according to claim 11, wherein the composition of the upper phase is 12–18% chloroform, 45–55% methanol and 25–40% water.

14. The method according to claim 13, wherein the composition of the upper phase is 15% chloroform, 52% methanol and 33% water.

15. The method according to claim 11, wherein the composition of the lower phase is 50–80% chloroform, 15–40% methanol and 2–8% water.

16. The method according to claim 15, wherein the composition of the lower phase is 68% chloroform, 27% methanol and 5% water.

17. A method of purifying mycolic acids or salts thereof consisting essentially of:
   a) saponifying a crude bacterial cellular extract comprising mycolic acids, salts thereof or derivatives thereof and contaminants to form a saponification mixture;
   b) extracting an extracted mixture from the saponification mixture, the extracted mixture comprising mycolic acids or salts thereof and contaminants;
   c) dissolving the extracted mixture in a bi-phasic solvent to form a dissolved mixture comprising the mycolic acids or salts thereof and contaminants;
   d) purifying the mycolic acids by subjecting the dissolved mixture to countercurrent distribution separation comprising a sufficient number of cycles to separate the mycolic acids or salts thereof from the contaminants; and
   e) removing the separated, purified mycolic acids or salts thereof or any methyl ester derivatives thereof which have formed during countercurrent distribution separation from the bi-phasic solvent and, optionally, extracting any residual impurities from the removed mycolic acids, salts thereof or methyl ester derivatives thereof with acetone.

18. A method of purifying mycolic acids, salts thereof or derivatives thereof, said method consisting essentially of:
   a) providing a mixture comprising the mycolic acids, salts thereof or derivatives thereof and contaminants;
   b) dissolving the mixture in a bi-phasic solvent to form a dissolved mixture comprising the mycolic acids, salts thereof or derivatives thereof and contaminants;
   c) purifying the mycolic acids, salts thereof or derivatives thereof by subjecting the dissolved mixture to countercurrent distribution separation comprising a sufficient number of cycles to separate the mycolic acids, salts thereof or derivatives thereof from the contaminants; and
   d) removing the separated, purified mycolic acids, salts thereof or derivatives thereof from the bi-phasic solvent and extracting any residual impurities from the removed mycolic acids, salts or derivatives thereof with acetone.

19. A method of purifying mycolic acids, salts thereof or derivatives thereof, said method consisting essentially of:
   a) providing a mixture comprising the mycolic acids, salts thereof or derivatives thereof and contaminants;
   b) dissolving the mixture in a bi-phasic solvent to form a dissolved mixture comprising the mycolic acids, salts thereof or derivatives thereof and contaminants;
   c) purifying the mycolic acids, salts thereof or derivatives thereof by subjecting the dissolved mixture to countercurrent distribution separation comprising a sufficient number of cycles to separate the mycolic acids, salts thereof or derivatives thereof from the contaminants; and
   d) removing the separated, purified mycolic acids, salts thereof or derivatives thereof from the bi-phasic solvent and saponifying the purified, separated mycolic acid derivatives after removal from the bi-phasic solvent.

20. A method of purifying mycolic acids, salts thereof or derivatives thereof, said method consisting essentially of:
   a) providing a mixture comprising the mycolic acids, salts thereof or derivatives thereof and contaminants;
   b) dissolving the mixture in a bi-phasic solvent to form a dissolved mixture comprising the mycolic acids, salts thereof or derivatives thereof and contaminants;
   c) purifying the mycolic acids, salts thereof or derivatives thereof by subjecting the dissolved mixture to countercurrent distribution separation comprising a sufficient number of cycles to separate the mycolic acids, salts thereof or derivatives thereof from the contaminants; and
   d) removing the separated, purified mycolic acids, salts thereof or derivatives thereof from the bi-phasic solvent and (i) extracting any residual impurities from the removed mycolic acids, salts or derivatives thereof with acetone and (ii) saponifying the purified, separated mycolic acid derivatives after removal from the bi-phasic solvent.

21. The method according to claim 18 wherein the mixture provided in (a) is a saponified mixture comprising mycolic acids or salts thereof and contaminants.

22. The method according to claim 19 wherein the mixture provided in (a) is a saponified mixture comprising mycolic acids or salts thereof and contaminants.

23. The method according to claim 20 wherein the mixture provided in (a) is a saponified mixture comprising mycolic acids or salts thereof and contaminants.

24. The method according to claim 1, wherein the mixture provided in step (a) consists essentially of mycolic acids and contaminants.

* * * * *